US011497656B2

(12) United States Patent
Brown et al.

(10) Patent No.: US 11,497,656 B2
(45) Date of Patent: Nov. 15, 2022

(54) TAMPON AND METHOD FOR MAKING THE SAME

(71) Applicant: The Procter & Gamble Company, Cincinnati, OH (US)

(72) Inventors: Henry A. Brown, Cincinnati, OH (US); Ryo Minoguchi, Cincinnati, OH (US); Lymarie Semidey-Flecha, West Chester, OH (US); Gerard A. Viens, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1084 days.

(21) Appl. No.: 15/805,508

(22) Filed: Nov. 7, 2017

(65) Prior Publication Data

US 2018/0125724 A1 May 10, 2018

Related U.S. Application Data

(60) Provisional application No. 62/418,496, filed on Nov. 7, 2016.

(51) Int. Cl.
*A61F 13/15* (2006.01)
*A61F 13/20* (2006.01)
*A61F 13/34* (2006.01)

(52) U.S. Cl.
CPC .... *A61F 13/2051* (2013.01); *A61F 13/15203* (2013.01); *A61F 13/2028* (2013.01);
(Continued)

(58) Field of Classification Search
CPC .............. A61F 13/2051; A61F 13/2028; A61F 13/2091; A61F 13/15203
See application file for complete search history.

(56) References Cited

U.S. PATENT DOCUMENTS 1,731,665 A 10/1929 Huebsch
1,964,911 A 7/1934 Haas
(Continued)

FOREIGN PATENT DOCUMENTS

DE 29615883 U1 3/1997
EP 1064901 A2 1/2001
(Continued)

OTHER PUBLICATIONS

Search Report and Written Opinion for PCT/US2015/040872 dated Oct. 30, 2015.
(Continued)

*Primary Examiner* — Jacqueline F Stephens
(74) *Attorney, Agent, or Firm* — Amanda Herman Berghauer; William E. Gallagher; George H. Leal

(57) ABSTRACT

An absorbent tampon is disclosed herein. The absorbent tampon has a fiber integrated primary absorbent member having an insertion end and a withdrawal end disposed opposite the insertion end, a top portion and a bottom portion as determined by the Secondary Desorption Performance method, and a secondary absorbent member attached to the primary absorbent member and extending outboard of the withdrawal end of the primary absorbent member. The tampon exhibits a wet weight percentage fluid in the bottom portion of at least about 60 percent when measured in accordance with the Secondary Desorption Performance method.

16 Claims, 24 Drawing Sheets

(52) U.S. Cl.
CPC ........ *A61F 13/2091* (2013.01); *A61F 13/208* (2013.01); *A61F 13/34* (2013.01); *A61F 2013/15406* (2013.01); *A61F 2013/15463* (2013.01)

(56) References Cited

U.S. PATENT DOCUMENTS

| | | | |
|---|---|---|---|
| 2,123,750 A | 7/1938 | Schulz | |
| 2,412,391 A | 12/1946 | Crockford | |
| 2,566,190 A | 8/1951 | Greiner | |
| 3,013,558 A | 12/1961 | Leupoid | |
| 3,037,506 A | 6/1962 | Penksa | |
| 3,058,469 A | 10/1962 | Crockford | |
| 3,101,714 A | 8/1963 | Penksa | |
| 3,135,262 A | 6/1964 | Kobler | |
| 3,420,234 A | 1/1969 | Phelps | |
| 3,431,909 A | 3/1969 | Krusko | |
| 3,572,341 A | 3/1971 | Glassman | |
| 3,628,534 A | 12/1971 | Donohue | |
| 3,674,029 A | 7/1972 | Bates et al. | |
| 3,732,866 A | 5/1973 | Accavallo | |
| 3,738,364 A | 6/1973 | Brien et al. | |
| 3,854,481 A | 12/1974 | Messing | |
| 3,905,372 A | 9/1975 | Denkinger | |
| 3,948,257 A | 4/1976 | Bossak | |
| 3,965,905 A | 6/1976 | Schoenholz et al. | |
| 3,995,636 A | 12/1976 | Murray et al. | |
| 4,077,408 A | 3/1978 | Murray et al. | |
| 4,217,900 A | 8/1980 | Wiegner et al. | |
| 4,326,527 A | 4/1982 | Wollangk et al. | |
| 4,536,175 A | 8/1985 | Arnold | |
| 5,047,024 A | 9/1991 | Glassman | |
| 5,112,348 A | 5/1992 | Glassman | |
| 5,659,934 A | 8/1997 | Jessup et al. | |
| 5,718,675 A | 2/1998 | Leijd | |
| 5,800,338 A | 9/1998 | Kollerup et al. | |
| 6,039,716 A | 3/2000 | Jessup et al. | |
| 6,142,984 A | 11/2000 | Brown et al. | |
| 6,186,994 B1 | 2/2001 | Bowles | |
| 6,433,246 B1 | 8/2002 | Nguyen et al. | |
| 6,554,814 B1 | 4/2003 | Agyapong et al. | |
| 6,635,800 B2 | 10/2003 | Jackson et al. | |
| 6,740,070 B2 | 5/2004 | Agyapong et al. | |
| 6,887,226 B2 | 5/2005 | Cassoni et al. | |
| 2002/0133133 A1 | 9/2002 | Agyapong et al. | |
| 2003/0225389 A1 | 12/2003 | Cassoni | |
| 2005/0055003 A1 | 3/2005 | Bittner et al. | |
| 2006/0247592 A1 | 11/2006 | Schmidt-Forst et al. | |
| 2007/0073257 A1* | 3/2007 | Buck | A61F 13/2082 604/385.18 |
| 2010/0076393 A1 | 3/2010 | Wasson et al. | |
| 2011/0184332 A1* | 7/2011 | Minoguchi | A61F 13/2077 604/11 |
| 2012/0238990 A1* | 9/2012 | Jackson | A61F 13/2094 604/385.201 |
| 2012/0283684 A1* | 11/2012 | Schmidt-Foerst | A61F 13/2088 604/385.17 |
| 2013/0160259 A1 | 6/2013 | McDaniel et al. | |
| 2014/0115845 A1 | 5/2014 | Tomsovic et al. | |
| 2015/0173966 A1 | 6/2015 | Schickli et al. | |
| 2016/0015572 A1* | 1/2016 | Viens | A61F 13/2065 604/385.18 |
| 2019/0133836 A1 | 5/2019 | Semidey-flecha | |

FOREIGN PATENT DOCUMENTS

| | | |
|---|---|---|
| GB | 2225949 A | 6/1990 |
| JP | S6173317 U | 5/1986 |
| JP | 02028900 | 8/1990 |
| JP | 2002521133 A | 7/2002 |
| WO | 0200001338 | 1/2000 |
| WO | WO2000061052 A1 | 10/2000 |
| WO | WO2007001216 A1 | 1/2007 |

OTHER PUBLICATIONS

Search Report and Written Opinion for PCT/US2017/060370 dated Jan. 18, 2018.
Search Report and Written Opinion for PCT/US2017/060350 dated Jan. 12, 2018.
All Office Actions for U.S. Appl. No. 14/801,871, filed Jul. 17, 2015.
All Office Actions for U.S. Appl. No. 15/805,415, filed Nov. 7, 2017.

* cited by examiner

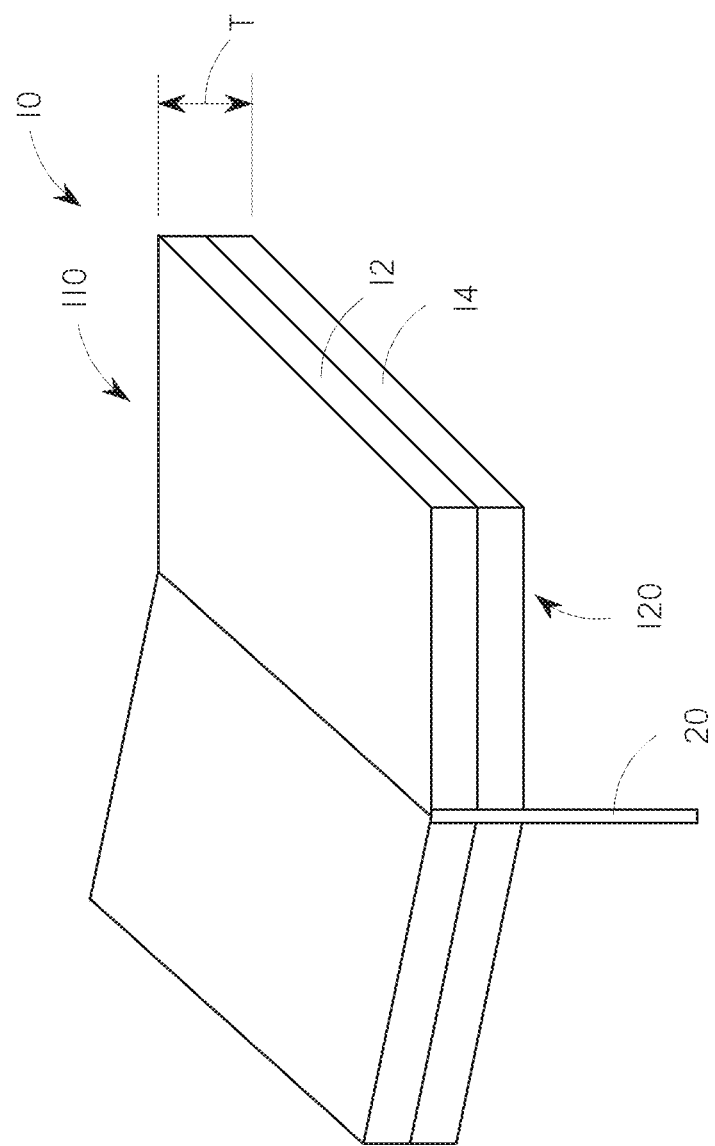

TAMPON AND METHOD FOR MAKING THE SAME

FIELD OF THE INVENTION

The present disclosure relates to tampons and methods for making tampons.

BACKGROUND OF THE INVENTION

Tampons are widely used by consumers during menstruation. Because tampons typically offer a more discreet alternative to pads in absorbing menses, many consumers prefer tampons to pads. Generally, tampons consist of an absorbent pledget and a withdrawal cord attached to the absorbent pledget. The absorbent pledget has an insertion end (top) and an opposing withdrawal end (bottom). The withdrawal cord extends from the withdrawal end. The absorbent pledget is typically compressed to a small size to enable simple and comfortable insertion. Once inserted into the vagina, the absorbent pledget must then expand in order to reduce the likelihood of leakage.

There are typically two types of leakage associated with tampons, i.e. bypass and kinetic. Bypass leakage occurs when the absorbent pledget does not expand enough from its initial compressed state to make contact with the vaginal walls. As some of the menstrual fluid may run along the vaginal wall, the failure of the pledget to contact the vaginal wall can allow this fluid to bypass the pledget to the vaginal opening and leak therefrom. In general, expansion near the withdrawal end of pledget can reduce the likelihood of bypass leakage. However, in order to expand, fluid absorbed by the pledget must be transferred to the withdrawal end of the pledget. Unfortunately, the movement of fluid along the pledget from the insertion end to the withdrawal end can lead to kinetic leakage. Moreover, even where fluid is transferred to the withdrawal end of the pledget, the pledget may not be able to expand to a sufficient amount to contact the vaginal walls.

As noted previously, while the transfer of fluid from the insertion end to the withdrawal end can drive expansion of the pledget at the withdrawal end, additional transfer of absorbed fluid to the withdrawal end can over saturate the pledget in the withdrawal end. This can lead to kinetic leakage. Unfortunately, kinetic leakage can be exacerbated by gravity when the user is in an upright position.

Conventional tampons may address either kinetic or bypass leakage, but the requirements in addressing these two leakage mechanisms are in conflict. For example, if fluid is too rapidly transported along the pledget to the withdrawal end, the likelihood of kinetic leakage may increase. In contrast, if the fluid is transported too slowly along the pledget, while the likelihood of kinetic leakage is reduced, the likelihood of bypass leakage is increased. What is needed is a tampon that can better address the two leakage mechanisms described above.

SUMMARY OF THE INVENTION

Tampons of the present disclosure can achieve a good balance of fluid distribution and expansion to reduce the likelihood kinetic leakage as well as bypass leakage. In some forms, an absorbent tampon comprises a fiber integrated primary absorbent member and a secondary absorbent member. The primary absorbent member has an insertion end and a withdrawal end disposed opposite the insertion end, a top adjacent the insertion end, a bottom adjacent the withdrawal end, and a middle disposed between the top and the bottom. The primary absorbent member further comprising a top portion and a bottom portion as determined by the Secondary Desorption Performance test. The secondary absorbent member is attached to the primary absorbent member and extends outboard of the withdrawal end of the primary absorbent member, the secondary absorbent member. And, wherein the tampon exhibits a wet weight percentage fluid in the bottom portion of greater than 60 percent.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 1A is a perspective view of an exemplary tampon pledget of the present invention.

DETAILED DESCRIPTION OF THE INVENTION

Figure 1B:
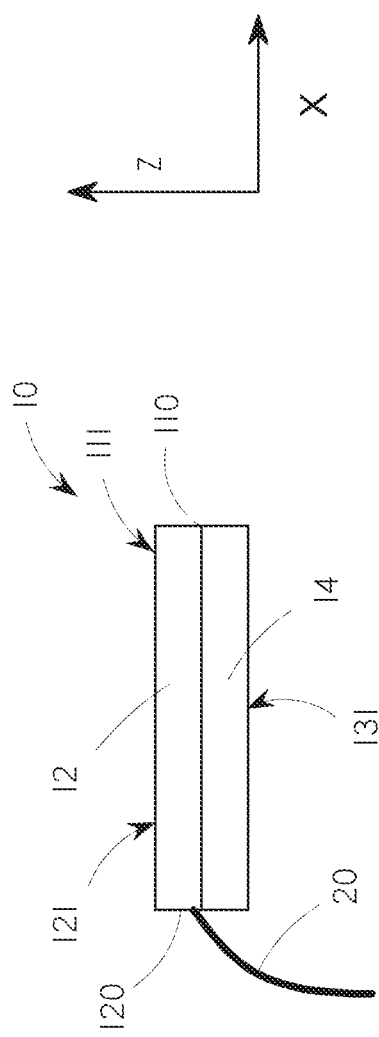
FIG. 1B is a side view of the tampon pledget of FIG. 1A.

The following text sets forth a broad description of numerous different forms of the present invention. The description is to be construed as exemplary only and does not describe every possible form since describing every possible form would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative forms could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112 (f).

As used herein, the terms "pledget" and "tampon pledget" refer to a mass of absorbent material prior to compression of such material into tampon as described below. Tampon pledgets are sometimes referred to as a tampon blank, or a softwind.

As used herein, the term "tampon" refers to any type of absorbent structure which is inserted into the vaginal canal or other body cavities for the absorption of menses or other bodily exudates. Tampons typically are constructed from an absorbent material which has been compressed in any or all of the width direction, the radial direction, and the axial direction, in order to provide a tampon which is of a size and stability to allow insertion within the vagina or other body cavity. A tampon which has been so compressed is referred to herein as having a "self-sustaining" form. That is, the degree of compression and or conditioning of the absorbent material results in a tampon that will tend to retain its general shape and size prior to insertion into the body. The tampons of the present invention are "fluid-expanding" tampons that expand or uncompress upon contact and absorption of fluid. Fluid expanding tampons are contrasted to "mechanically expanding" tampons that may use springs or some other mechanical supplier of force to expand. An example of such a mechanically expanding tampon is described in U.S. Pat. No. 3,706,311 to Kohx et al.

The "Syngyna" test is an industry standard tampon absorbency capacity test. The apparatus and method for performing this tampon absorbency test are provided in 21 United States Code of Federal Regulation 801.430. In the United States and other regions, tampons carry standardized absorbency labels according to Syngyna test absorbency ranges. Tampons absorbing 6 to 9 grams are labeled "regular absorbency," and tampons absorbing 9 to 12 grams are labeled "super absorbency."

Tampon expansion and expansion rates are calculated with the dynamic expansion test that includes a few variations from the standard Syngyna test and that is described in greater detail towards the end of the instant specification in the Test Methods section.

Figure 1C:
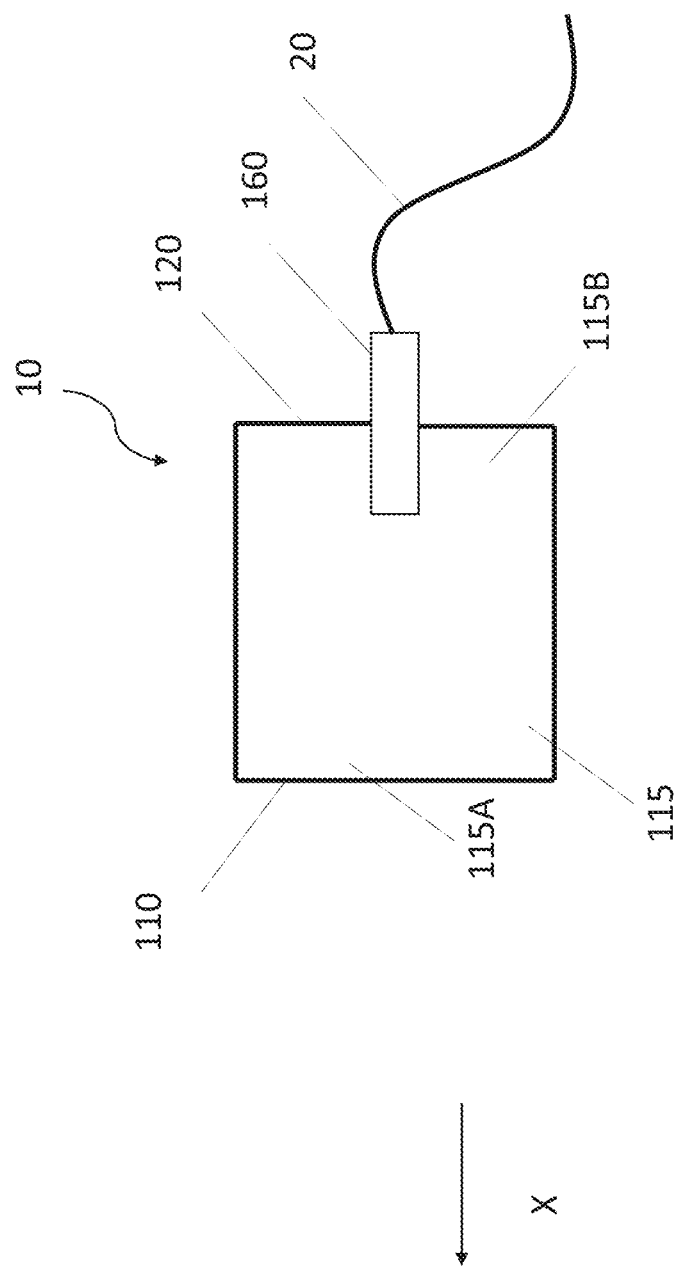
FIG. 1C is a plan view showing the tampon pledget of FIG. 1A.

Tampons of the present disclosure are formed from a mass of absorbent material which forms a primary absorbent member 115 and a secondary absorbent member 160 attached to the primary absorbent member 115. The mass of absorbent material is generally in the form of one or more layers of fibrous materials. As noted above, the uncompressed primary absorbent member is sometimes called a pledget or tampon blank. FIGS. 1A-1C show an exemplary tampon pledget 10 comprising an insertion end 110 and a withdrawal end 120. As shown, the pledget 10 further comprises two layers of absorbent materials 12 and 14 that combine to define a pledget thickness T; and a withdrawal string 20. Additionally, the tampon comprises a secondary absorbent member 160 extending outboard of the withdrawal end 120. In some forms, the secondary absorbent member 160 may be in the form of a braid to which a withdrawal string 20 is attached—discussed hereafter. Forms of the present invention are contemplated where any suitable number of layers may be utilized—for example, one layer, two layers, three layers, four layers, five layers, six layers, seven layers, and so on. Additionally, the pledget 10 comprises an X-direction which is generally parallel to a long axis of the pledget 10 and a Z-direction which is generally perpendicular to the X-direction.

With regard to FIGS. 1B and 1C, a top 111 of the pledget 10 is disposed adjacent the insertion end 110 and a bottom 121 of the pledget 10 is disposed adjacent the withdrawal end 120. A middle 131 is disposed between the top 111 and the bottom 121 of the pledget 10. The primary absorbent member 115 in the X direction comprises a top portion 115A and a bottom portion 115B. The top portion 115A and the bottom portion 115B are determined via mass as described with regard to the Secondary Desorption Performance test method described herein. As shown, the secondary absorbent member 160 may be attached in the bottom portion 115B of the primary absorbent member 115, in some forms. In some forms, the secondary absorbent member 160 may extend into the top portion of the primary absorbent member 115. In some forms, the secondary absorbent member 160 may extend the full length of the primary absorbent member 115.

Figure 1D:
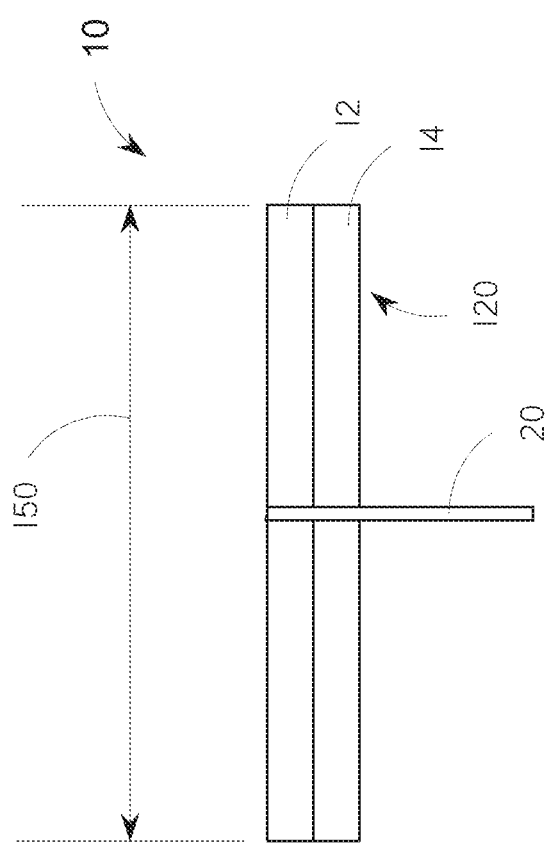
FIG. 1D is an elevation view of the tampon pledget of FIG. 1A.

Referring now to FIG. 1D, pledget 10 of the present disclosure expands upon fluid insult to eventually an expanded width 150. In some forms, a tampon of the present invention which may be sold as a "Regular" absorbent tampon may comprise a mass of absorbent material which has been compressed into a generally cylindrical, self-sustaining form. The resulting tampon has an absorbent capacity as measured by the standard Syngyna test of between about 6 to about 9 grams. The tampon is fluid expanding and may have an expanded width 150 upon fluid absorption of at least about 17 mm.

In some forms, a tampon of the present invention may be sold as a "Super" absorbency tampon. Such a tampon may comprise a mass of absorbent material which has been compressed into a generally cylindrical, self-sustaining form. Subsequent to this compression, the absorbent material may have a diameter of less that about 19 mm. The resulting tampon has an absorbent capacity as measured by the standard Syngyna test of between about 9 to about 12 grams. The tampon is fluid expanding and preferably has an expanded width 150 upon fluid absorption of at least about 18 mm.

To create a better performing tampon requires solving the balance of two parameters, i.e. expansion potential vs. fluid absorption kinetics. Conventional tampon designs often sought to enhance tampon protection via maximization of one of these parameters while unintentionally negatively impacting the other. For example, to make a tampon expand more quickly at the critical bottom area of the tampon, tampons were designed to quickly move fluid to the bottom of the tampon, however this created a design that also allowed the fast moving fluid to seep out of the bottom, i.e. kinetic leakage. In contrast, if a designer sought to better hold onto the fluid, changes could be made that would unintentionally negatively impact the ability to expand the tampon at the bottom and therefore increase the likelihood of bypass leakage. Tampons of the present disclosure can solve this contradiction in performance parameters.

In order to create the desired properties of the present disclosure, the absorbent material of the pledget 10 comprises fiber integrated nonwoven material. Fiber integration of a nonwoven material can occur via any suitable process which entangles fibers primarily in a Z-direction (positive or negative). Exemplary processes which are amenable in creating such fiber integration include needlepunching and spunlacing. Needlepunching involves the mechanical interlocking of fibers of a spunbonded or carded web. In the needlepunching process, a plurality of barbed needles repeatedly pass in and out of a nonwoven web and push fibers of the nonwoven web in a positive and/or negative Z-direction. In contrast, the spunlace process uses high-speed jets of water to cause the interlocking of fibers of a nonwoven web. The high-speed jets of water push fibers of the nonwoven web in the positive or negative Z-direction. So, in some forms of the present invention, at least one of the layers of the absorbent material comprises fiber integrated nonwoven material. In some forms, each of the layers of the absorbent material comprise fiber integrated nonwoven material.

The absorbent material pledget may comprise one layer or a plurality of layers. For example, for those forms where the absorbent material pledget comprises one layer and sufficient fiber integration as described herein, the single layer can achieve the desired properties. Similarly, where the absorbent material pledget comprises a plurality of layers, each of the layers may individually comprise fiber integration. Or, in some forms, a plurality of layers may be fiber integrated together such that the layers are fiber integrated with one another.

However, the method of fiber integration can impact the structure of the absorbent material of the pledget 10. For example, for absorbent material that is needle punched, a tampon pledget 10 comprising 700 gsm of absorbent material can take on a variety of different forms. For example, the absorbent material may be configured as one layer, two layers, or more layers. In contrast, where the tampon pledget 10 comprises 700 gsm of absorbent material—where the absorbent materials spunlaced—more than one layer will likely be required. Spunlacing of absorbent material having a basis weight of 700 gsm would be difficult at best. In such forms, the absorbent material would comprise a plurality of layers each of which or at least a portion of which were spunlaced.

It is believed that the fiber integrated nonwoven material can create a balance between expansion potential and fluid absorption kinetics. In some forms, the fiber integrated nonwoven material of the tampons of the present disclosure provide good fluid distribution properties along the X direction (see FIG. 1B) allowing the bottom of the pledget to expand. Recall that this expansion of the bottom of the pledget can help reduce the likelihood of bypass leakage. At the same time however, the fiber integrated nonwoven material of the tampons of the present disclosure also provide good fluid distribution properties along the Z-direction (see FIG. 1B) such that the likelihood of kinetic leakage is also reduced. Without wishing to be bound by theory, it is believed that the fiber integration disclosed above, helps to create the Z-direction fluid distribution properties.

The inventors have surprisingly found that when there is sufficient Z-direction integration of the fibers of the layer(s), that a secondary absorbent member can help provide good fluid distribution along a bottom portion of the pledget. The method for determining the degree of Z-direction integration is discussed hereafter in the Test Methods section under the Z-cluster method which looks for groupings of Z-oriented fibers. Table 1 shows the results of the Z-cluster test.

TABLE 1

| | Sample Configuration: | | | |
|---|---|---|---|---|
| | Configuration 1 | Configuration 2 | Configuration 3 | Configuration 4 |
| Fiber Blend Ratio: | 75/25 (Rayon/Cotton) | 75/25 (Rayon/Cotton) | 100% Rayon | 100% Rayon |
| Area of 3$^{rd}$ largest Cluster (mm$^2$) | 0.0040 | 0.0633 | 0.0024 | 0.0442 |
| Avg. Area of Top 3 Cluster (mm$^2$) | 0.0125 | 0.0965 | 0.0027 | 0.0536 |

Multiple samples having configuration 1 were created and evaluated. Each of these samples comprised carded and calendared fiber nonwoven web with the fiber content as described in Table 1.

Multiple samples having configuration 2 were created in accordance with the present disclosure and evaluated. Each of these samples comprised the fiber blend ratio described in Table 1, with 3.3 dtex Galaxy™ tri-lobal, rayon fibers, having a basis weight of 547 gsm. The material for each of the samples of configuration 2 was needlepunched.

Multiple samples having configuration 3 were created and evaluated. Each of these samples comprise the fiber blend ratio described in Table 1, with 100 percent Galaxy™ tri-lobal, rayon fibers, having a basis weight of about 535 gsm.

Multiple samples having configuration 4 were obtained. Each of these samples was commercially available and sold under the trade name Walgreens™ Perfection Silk™ Regular.

In some forms, the area of the third largest cluster may be greater than about 0.01 mm$^2$, greater than about 0.02 mm$^2$, greater than about 0.03 mm$^2$, greater than about 0.05 mm$^2$, or greater than about 0.07 mm$^2$, specifically including all values within these ranges and any ranges created thereby.

In some forms, the average area of the top 3 clusters is greater than about 0.02 mm$^2$, greater than about 0.03 mm$^2$, greater than about 0.05 mm$^2$, greater than about 0.07 mm$^2$, or greater than about 0.09 mm$^2$, specifically including all values within these ranges and any ranges created thereby.

As noted previously, the absorbent material of the present invention may comprise one or more layers. In some forms, each of the plurality of nonwoven layers may have a basis weight of about 100 grams per square meter ("gsm"). In some forms, each of the plurality of fiber integrated nonwoven layers may be at a basis weight of greater than about 20 gsm, greater than about 30 gsm, greater than about 40 gsm, greater than about 50 gsm, greater than about 60 gsm, greater than about 70 gsm, greater than about 75 gsm, greater than about 80 gsm, greater than about 85 gsm, greater than about 90 gsm, greater than about 95 gsm, greater than about 100 gsm, greater than about 110 gsm, greater than about 120 gsm, greater than about 130 gsm, greater than about 140 gsm, greater than about 150 gsm, greater than about 160 gsm, greater than about 170 gsm, greater than about 180 gsm, greater than about 190 gsm, or less than about 200 gsm or any ranges encompassed by these values and/or any number within these values.

Regardless of whether the absorbent material comprises multiple layers or one layer, the cumulative basis weight of the absorbent material may be between about 200 gsm and 1300 gsm. For example, the cumulative basis weight of the absorbent material 12 may be greater than about 200 gsm, greater than about 300 gsm, greater than about 400 gsm, greater than about 500 gsm, greater than about 600 gsm, greater than about 700 gsm, greater than about 800 gsm, greater than about 900 gsm, greater than about 1000 gsm, greater than about 1100 gsm, or less than or equal to about 1200 gsm. Forms are contemplated wherein the cumulative basis weight of the absorbent material comprises a range encompassed by the values above and/or wherein the cumulative basis weight of the absorbent material is a number within the values provided above.

Based on the present disclosure, the skilled artisan should appreciate that the mass of absorbent material of the pledget may be any suitable shaped, size, material, or construction. While pledget 10 is shown having a generally rectangular shape, other shapes are possible, including, for example, chevron, trapezoidal, triangular, semi-circular, "bow-tie", cross, and H.

Tampons of the present disclosure can be compressed into a generally cylindrical, self-sustaining form in the width direction, the radial direction, the axial direction, or any combination of these directions. Alternative compression directions can also be used. The pledgets can be compressed to a density ranging from about 0.25 to about 0.45 grams per cubic centimeter. The method for determining tampon density is provided below in the Test Methods section. In preferred embodiments, the pledgets are compressed to a density of greater than 0.35 grams per cubic centimeter, or a density of greater than 0.4 grams per cubic centimeter. For comparison, the assignee of the present invention currently manufactures TAMPAX brand tampons, wherein the regular and super absorbency versions have a density of around 0.33 grams per cubic centimeter.

The setting of the compressed pledgets is believed to play a critical role in the expansion profile of the tampon pledget. Compressed tampon pledgets tend to re-expand to their original dimension. To overcome this tendency, heat-setting is utilized. However, thermal setting of compressed pledgets can lessen the absorptive capacity of the pledgets if not done correctly. Some suitable methods of setting or stabilizing the tampon size and shape include heating a compressed pledget via microwaving as disclosed in U.S. Patent Application Ser. No. 62/338,776 and Ser. No. 15/159,316. Preferably, the compressed pledget is subject to a conditioning via a microwave source for up to 25 seconds. The power of the microwave can be 2000-6000 Watts.

Forms of the present invention are also contemplated where the absorbent pledgets are subjected to steam or thermal gradient conduction as described in U.S. Pat. No. 7,047,608. Additional forms are contemplated where a heated gas or other medium can be applied to the compressed pledget via at least one pore or fluid communication passage while the compressed pledget is within a closed compression mold cavity.

As discussed previously, tampons of the present disclosure may comprise a secondary absorbent. There are conventional tampons on the market that have secondary absorbents. These tampons utilize a carded calendared webs in their primary absorbents. These carded calendared webs comprise fibers mainly oriented in the X-direction.

Without wishing to be bound by theory, it is believed that during bypass leakage, the secondary absorbent can capture the bypass leakage. And, the secondary absorbent can then wick the bypass leakage into a secondary loading zone at the bottom of the pad. For conventional materials, the secondary loading zone is near the middle of the primary absorbent member. However, for the carded webs of conventional tampons, since fluid moves along the fibers, absorbed fluid by the secondary has to move against gravity to free up storage for future loading at the secondary loading zone. A more even distribution of fiber orientations would allow the captured fluid to move perpendicular to the force of gravity to leverage available storage lower in the primary absorbent. It is also believed that more fibers oriented in the Y and Z-directions, leads to a lower kinetic leakage, as fluid can travel more effectively perpendicular to gravity and is therefore less likely to travel in the X-direction up or down the primary absorbent. And it is believed that when fluid is moved perpendicular to the force of gravity (perpendicular to the X-direction), less work is required to distribute fluid. Additionally, it is believed that such distribution can encourage expansion of the primary absorbent near the bottom of the primary absorbent. Such expansion can help reduce the likelihood of future bypass leakage. So, the trade-off between bypass leakage and kinetic leakage may be overcome, by using the secondary absorbent to provide captured fluid to the fiber integrated primary absorbent.

Table 2 shows data regarding the benefits of a secondary absorbent member on a fiber integrated primary absorbent versus carded primary absorbents.

TABLE 2

| Pad construction | Secondary Option | | | | | |
|---|---|---|---|---|---|---|
| | Option 1 | | Option 2 | | Option 3 | |
| | Carded | NP | Carded | NP | Carded | NP |
| Uptake (g) | 4.30 | 4.13 | 3.69 | 3.21 | 5.53 | 4.68 |
| Fluid in bottom (g) | 2.45 | 2.76 | 2.22 | 2.33 | 3.16 | 2.33 |
| % Fluid in bottom | 56.9% | 67.0% | 59.9% | 72.4% | 57.1% | 72.4% |

As shown, the secondary absorbent members of the present disclosure, when coupled with primary absorbent members having Z-direction integration, retained more fluid in the bottom portion of the absorbent pad than their conventional carded counterparts with the secondary absorbent member. For the above data the secondary options were as described below.

Each of Options 1, 2, and 3 comprised a primary absorbent member and a secondary absorbent member. Each of the secondary absorbent members comprised polypropylene fibers that were braided/weaved in a removal cord. The polypropylene fibers are tinted in blue and coated with hydrophilic surfactant. Average length of the secondary absorbent is about 48 mm, including portions on the primary absorbent and off the primary absorbent. An average width at the midpoint along the longitudinal axis is about 7 mm. For Option 1, the secondary absorbent was created and attached to the primary absorbent of Option 1 as described below. For Option 2, the secondary absorbent was removed from Tampax™ Pearl™ Regular commercially available product and hand sewn to the primary absorbent of Option 2. For Option 3, the secondary absorbent was removed from Tampax™ Pearl™ Super commercially available product and hand sewn to the primary absorbent of Option 3.

The primary absorbent for Option 1 comprised two variants. The first variant was a carded, calendared, fiber web having a fiber blend ratio of 75 percent Galaxy™ tri-lobal, rayon, and 25 percent cotton, where the fiber web had a basis weight of about 562 gsm. The second variant was a needlepunched web having a fiber blend ratio of 75 percent Galaxy™ tri-lobal, rayon, and 25 percent cotton, where the needlepunched web had a basis weight of about 553 gsm.

The primary absorbent for Option 2 comprised two variants. The first variant was a carded, calendared, fiber web having the fiber blend ratio of Option 1 and a basis weight of 548 gsm. The second variant was a needlepunched web having a fiber blend ratio of Option 1 and a basis weight of about 547 gsm.

The primary absorbent for Option 3 comprised two variants. The first variant and the second variant were as described with regard to Option 2 for the first variant and the second variant, respectively.

As demonstrated in Table 2, where needlepunch primary absorbent members were utilized in conjunction with a secondary absorbent member, more fluid was retained in the bottom portion of the primary absorbent member. In some forms, a percent fluid in the bottom portion of the primary absorbent member may be greater than 60 percent, greater than 65 percent, greater than 67 percent, greater than 70 percent, greater than 72 percent, or greater than about 74 percent, specifically including all values within these ranges and any ranges created thereby.

And as noted previously, the fibers of the secondary absorbent member may comprise a hydrophilic surfactant. Any suitable surfactant may be utilized.

In some forms, the mass of secondary absorbent material is integral with the primary absorbent member prior to compression of the pledget. In some forms, the secondary absorbent material is not compressed; or, if compressed, is not compressed to the same degree as the primary absorbent member. In some forms, the density of material which comprises the mass of secondary absorbent material is lower than the density of the primary absorbent member.

The secondary absorbent member may comprise one piece of material as shown, for example, in FIG. 1C, or may comprise multiple discrete pieces. The secondary absorbent member may be arranged in a wide variety of shapes and configurations and may be generally cylindrical, spherical, semi-spherical, disc-like, planar, rectangular, "skirt-like" in shape, or may comprise "tufts" or whips of absorbent elements.

The size of the secondary absorbent member may vary according to its shape. For example, the mass of secondary absorbent member may be generally cylindrical and elongated. The length of the mass of secondary absorbent is measured in the direction generally parallel to a line running through the axis of the tampon extending through the insertion end and withdrawal end of the primary absorbent member. The length of the mass of secondary absorbent material may be between about 10 mm and about 55 mm, more preferably 25 mm and about 35 mm.

Any suitable amount of fiber may be used for the mass of secondary absorbent material. In some forms, about 0.05 g of absorbent fiber is used. The mass of secondary absorbent material may be constructed such that it will remain flexible, in order to facilitate comfort in use. The mass of secondary absorbent material may be joined to the primary absorbent member at any suitable location generally proximate the withdrawal end of the primary absorbent member. In some forms, the mass of secondary absorbent material may be joined to the withdrawal cord and is generally centered axially around the cord. It is also possible to attach such a mass of secondary absorbent material to the withdrawal end of the primary absorbent member either in addition to, or in lieu of, attachment to the withdrawal cord. In some particular forms, the mass of secondary absorbent material is joined to the withdrawal cord.

The mass of secondary absorbent material may be joined to the withdrawal cord (or other withdrawal mechanism) or the withdrawal end of the primary absorbent member, or both, by any variety of means. For example, the mass of secondary absorbent material may be joined to one or both of the withdrawal cord or the withdrawal end of the primary absorbent member using any suitable adhesive. Such adhesive may extend continuously along the length of attachment or it may be applied in a "dotted" fashion at discrete intervals. Alternatively, the mass of absorbent material may be joined to the withdrawal cord or primary absorbent member by stitching. Such stitching may use cotton or rayon thread. Other attachment mechanisms include thermally bonding (for example where the mass of secondary absorbent material has thermally bonded fibers or other thermally bonding materials incorporated therein), fusion bonding, or any other suitable means known in the art for joining such materials.

The mass of secondary absorbent material may be constructed from any of the materials described above for suitable as use in the primary absorbent member. A layer or sheet of secondary absorbent material may be formed independently of the primary absorbent member and slipped around the withdrawal cord and attached thereto. The withdrawal cord could be wound with an absorbent material, fiber, yarn, or other structure, in at least the portion of the cord located proximate to the withdrawal end of the primary absorbent member. In some forms, as mentioned previously, the secondary absorbent may comprise polypropylene fibers or any other suitable thermoplastic fibers. In some forms, as noted previously, the secondary absorbent member may comprise constituent material that is hydrophobic or may comprise constituent material that is hydrophilic.

The mass of secondary absorbent material may also be integral with any other component of the tampon. For example, the mass of secondary absorbent material may comprise an extension of the primary absorbent member (although preferably a less compressed portion). The mass of secondary absorbent material may be in the form of a sheet or layer of absorbent material. Additionally, in some forms, the withdrawal mechanism itself could serve as both such a withdrawal mechanism and the secondary absorbent material. An example of such an embodiment is a ribbon of material which serves as the withdrawal mechanism. The upper portion of this ribbon could be absorbent and serve as the mass of secondary absorbent material while the lower portion of such ribbon is non-absorbent. Additional details regarding the secondary absorbent can be found in U.S. Pat. No. 6,599,279.

Figure 2:
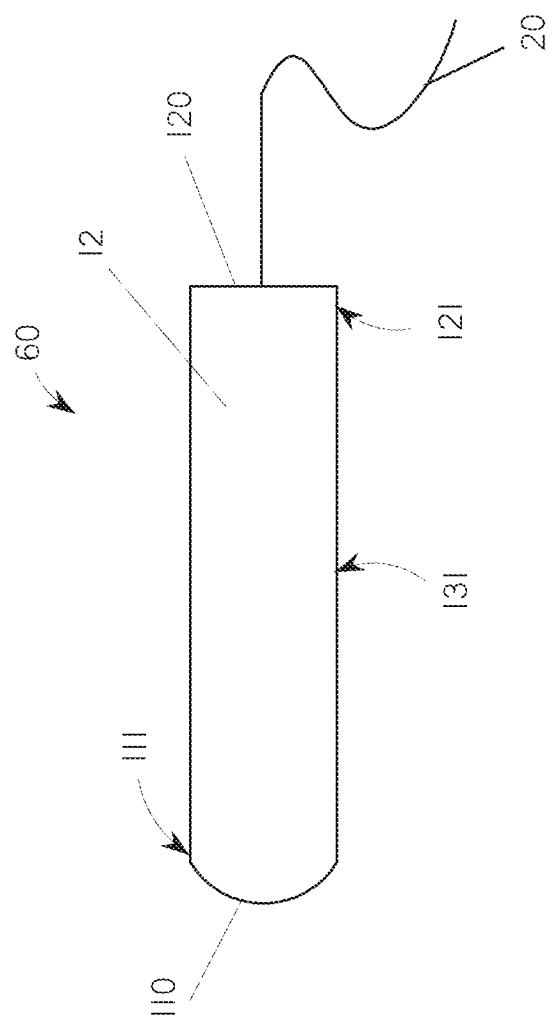
FIG. 2 is a side view of an exemplary tampon pledget that has been compressed.

FIG. 2 shows an exemplary tampon 60 having a generally cylindrical, self-sustaining form. Withdrawal strings useful in the present invention can be made of any suitable material known in the prior art, such as, e.g., cotton and rayon. A conventional type of withdrawal cord (in terms of thickness, material composition, etc.) may be periodically braided with a thicker slub of absorbent fibrous material, which acts as an absorbing member, to form a structure to be connected to the remaining of the tampon. In such forms, the portion of the cord, which will act as the withdrawal cord, may be treated to make it non-absorbent or even hydrophobic. It may also be a withdrawal cord as described in commonly assigned and co-pending U.S. application Ser. No. 09/309,467, filed on May 10, 1999 in the name of Taylor, et al.

The pledget may be constructed from a wide variety of liquid-absorbing materials commonly used in absorbent articles such as, for example, rayon, cotton, or comminuted wood pulp which is generally referred to as airfelt. Examples of other suitable absorbent materials include creped cellulose wading; meltblown polymers including coform; chemically stiffened, modified or cross-linked cellulosic fibers; synthetic fibers such as crimped polyester fibers; foam; paper; superabsorbent materials; absorbent gelling materials or combinations of mixtures of these. Preferably, the absorbent materials include rayon, cotton, or a combination thereof. In one embodiment, 100% rayon is employed because rayon has a slightly higher absorbency per weight in comparison to cotton and therefore a smaller tampon can be produced on a fixed tampon absorbency. Other forms are contemplated where the pledget comprises a blend of cotton and rayon, e.g. 50/50; 100/0; 75/25; 25/75; 60/40; 40/60; 20/80; 0/100, specifically including all values within these ratios or any ranges created thereby.

The tampon pledget may be compressed or may be manipulated further prior to compression. For example, the mass of absorbent material may for example be rolled, folded, or otherwise altered in profile to help with compression and/or affect the expansion properties during use.

A liquid permeable overwrap may also be placed over some or all of the mass of absorbent material prior to compression. The overwrap may have liquid permeable material, if desired. Such materials may comprise rayon, cotton, bi-component fibers, or other suitable natural or synthetic fibers known in the art. Rayon, polyethylene, polypropylene and blends of these are particularly suited for use as cover material. The synthetic fibers may include, but are not limited to, fibers such as polyester, polyolefin, nylon, polypropylene, polyethylene, polyacrylic, cellulose acetate or bi-component fibers. Natural fibers may include, but are not limited to, those commonly known to be non-synthetic and of natural origin such as cotton and/or rayon. In general, the natural fibers may provide ready absorption and fluid wicking strength. The synthetic fibers may balance the capillary strength of the blended material, enabling the tampon to more readily slip against moist tissue, resulting in easier removal and hence removal comfort. The overwrap may be fluid wicking and may extend beyond the withdrawal end of the absorbent material to form a skirt portion as described in U.S. Pat. No. 6,840,927, filed Nov. 16, 2001, entitled "Tampon with Fluid Wicking Overwrap With Skirt Portion," issued to Hasse, et al. Typically, the overwrap may extend from about 2 mm to about 30 mm beyond the withdrawal end of the absorbent material.

The ratio of synthetic fibers to natural fibers may fall in the range of from about 90:10 to about 30:70. Alternatively, the ratio of synthetic fibers to natural fibers may fall in the range of from about 70:30 to about 40:60. The synthetic fibers may have hydrophobic and/or hydrophilic surfaces. The synthetic fibers may be inherently hydrophilic, or may preferably be treated to provide such properties. The overwrap may comprise some level of hydrophobic fibers as well, as long as it does not significantly diminish the fluid wicking capacity of the overwrap of the tampon.

The blend of fibers forming the overwrap may be made by any number of techniques. The blends may be carded on webs. Commonly, carded webs that are hydroentangled, thermally bonded, and resin bonded all have application. In the latter case, the resin bonding agent may be used in place of the synthetic fibers as the method for tempering the aggressiveness of the natural fiber matrix. In this case, all natural fiber may be used with a significant amount of synthetic binder (10-30% by weight is common). Spunbond and meltblown processes, combining synthetic fibers extruded/spun onto/into a mat or carded web of natural fibers provide other acceptable techniques. The basis weight of the overwrap may fall into a range from about 10, 12 or 15 grams per square meter to about 30, 40, 50 or 60 grams per square meter. The materials for the tampon may be formed into a fabric, web, or batt that is suitable for use in the pledget by any suitable process such as airlaying, carding, wetlaying, or other known techniques.

Fluid pervious overwraps may be made by any number of known techniques, but is preferably an apertured nonwoven material. The nonwoven material may be made by carding, meltblowing, spunbonding, spunlacing, air laying, and the like. Aperturing may be accomplished by any known method, such as by hydroentangling on a suitable forming screen, such as, for example, the method described in U.S. Pat. No. 3,025,585. Aperturing may also be accomplished by various processes involving bonding and stretching, such as those described in U.S. Pat. Nos. 3,949,127; 4,588,360; 5,873,868. The apertures may be zoned as described in U.S. Pat. No. 7,994,387, filed on Oct. 17, 2007, entitled "Tampon having Zoned Apertured Overwrap," issued to Minoguchi, et al. In one embodiment, the apertures are formed by forming a plurality of spaced, melt stabilized regions, and then ring-rolling the web to stretch the web and form apertures in the melt stabilized regions, as described in U.S. Pat. Nos. 5,628,097 and 5,916,661, both of which are hereby incorporated by reference herein.

The tampons of the present disclosure can be inserted using an applicator; for example, tube and plunger type arrangements that can be plastic, paper, or other suitable material. The applicator may be flushable as described in U.S. Pat. No. 6,730,057, filed Mar. 16, 2001, entitled "Flushable Tampon Applicators," issued to Zhao, et al. The applicator may be corrugated as described in U.S. Pat. No. 7,066,870, filed Jun. 25, 2002, entitled "Method of Producing a Corrugated Tampon Applicator," issued to Fedyk, et al. The applicator may have a grip region as described in U.S. Pat. Nos. 8,303,558; 7,081,110; 8,449, 491; or 8,075,512. The applicator may have an absorbency indicator as described in U.S. Pat. No. 7,166,101, filed Dec. 9, 2005, entitled "Tampon Outer Surface Having Increasing Number of Written Identifiers to Indicate Absorbency," issued to Denti, et al. The applicator may have an improved cap that allows for a smooth and safe insertion of the tampon-applicator arrangement, the film cap must be such that it ruptures on a specific moment, when to specific low, maximum force is applied as described in U.S. Pat. No. 6,610, 025, filed Aug. 6, 2001, entitled "Tampon Applicator Arrangement," issued to Berg, et al. The cap may be in the form of petals as described in U.S. Pat. No. 6,652,477, filed Aug. 6, 2001, entitled "Tampon Applicator With Petals," issued to Karapasha, et al.

The tampon may be placed inside a wrapper. By 'wrapper material' it is meant herein any material suitable to be used for hygienically wrapping tampons. Said wrapper material has two surfaces; the 'inner surface' is directed towards the wrapped tampon, whereas the 'outer surface' is aligned opposite to said inner surface. Typically, suitable wrapper materials for use herein are flexible polymeric films, having a thickness of less than 1 mm. Examples for wrapper materials suitable for use are polymeric films made of polyethylene, polypropylene, polyester, cellophane, polyamide, poly(vinyl chloride), ethylene-vinyl acetate copolymer and the like. Alternatively, heat-shrinkable films, stretch films, pre-stretched elastic material, or combinations thereof may be used to create the wrapper. While not limited to a given composition, preferred compositions of heat-shrinkable and stretch films comprise primarily polyolefins such as polyethylene and polypropylene, or polyvinyl chloride. Polystyrene and polyethylene-terephthalate (PET), although being not heat sealable, are also suitable for use. Wrappers consisting of those materials can be closed by gluing with an adhesive. Other generally occlusive materials include metallic foils, such as aluminum foil. While occlusive wrapper materials are often preferred, in other situations non-occlusive or porous materials can be used, such as nonwovens, wovens, scrims, meshes and papers. Such non-occlusive materials can be made occlusive by combinations such as by lamination with or by coating with occlusive material. In the case of cellulosic papers, examples include lamination with a polymeric film such as a polyolefinic composition or coating or impregnation of the paper with wax. The aforementioned materials can be coated with various chemical compounds to improve their barrier properties or the ability for sealing. The wrapper may have a line of weakness or an improved opening means as described in U.S. Pat. No. 6,955,665, filed May 23, 2002, entitled "Tampon Wrapper with Improved Opening Means," issued to Domeier, et al. or U.S. Pat. No. 8,302,844, filed Nov. 20, 2006, entitled "Wrapper Having a Predetermined Line of Weakness," issued to McConnell, et al.

Fluid Kinetics:

Coupled with the above performance of the integrated primary absorbent and the secondary absorbent, in some forms, the fiber integrated primary absorbent can exhibit good fluid kinetics. The fluid kinetic value measures how quickly and how much fluid is moving in a selected area.

Currently marketed samples were obtained for several different brands of tampons. These currently marketed tampons were compared to tampons constructed in accordance with the present disclosure in a few tests discussed hereafter. The following is a description of the currently marketed tampon samples tested and the inventive samples tested.
Sample 1: Playtex™ Sport Unscented Super;
Sample 2: U by Kotex™ Click Compact Super;
Sample 3: Well at Walgreens™ Perfection Silk™ Plastic Super;
Sample 4: handmade tampons comprising the materials of Tampax® Pearl™, Super; and
Samples 5-13: comprised tampons constructed in accordance with the present disclosure and makeup the inventive samples. The absorbent material for each of samples 5-13 comprised either needle punched nonwoven material or spunlaced nonwoven material and were constructed to achieve a Syngyna within the super range designation as described herein.

Sample 5 comprised about 670 gsm of absorbent material in a single layer. The single layer absorbent material was needle punched to create the Z-direction fiber integration discussed herein. The absorbent material comprised 100% trilobal rayon fiber having a 3.3 dtex and 0.06% spin finish.

Sample 6 comprised 100% trilobal rayon fibers having 3.3 dtex and a 0.06% spin finish. The fibers were spunlaced. The fibers had a length of 38 mm. There were 7 layers in each of the Sample 6 samples where each of the layers had a basis weight of about 100 gsm plus/minus 7.

Sample 7 comprised a 50%/50% split of trilobal rayon fibers having a 3.3 dtex and round rayon fibers having a 3.0 dtex with a spin finish of 0.06%. Each of the fibers was 38 mm long. The fibers were spunlaced. There were 7 layers in each of the Sample 7 samples where each of the layers had a basis weight of about 100 gsm plus/minus 7.

Sample 8 comprised 100% round rayon fibers having a 3.0 dtex and a spin finish of 0.06%. The fibers were 38 mm long. The fibers were spunlaced. There were 7 layers in each of the Sample 8 samples where each of the layers had a basis weight of about 100 gsm plus/minus 7.

Sample 9 comprised 100% trilobal rayon fibers having a 4.5 dtex and a 0.06% spin finish. The fibers were 38 mm long and were spunlaced. There were 7 layers in each of the Sample 9 samples where each of the layers had a basis weight of about 100 gsm plus/minus 7.

Sample 10 comprised 100% trilobal rayon fibers having 3.3 dtex and a 0.12% spin finish. The trilobal fibers were spunlaced. The fibers had a length of 38 mm. There were 7 layers in each of the Sample 10 samples where each of the layers had a basis weight of about 100 gsm plus/minus 7.

Sample 11 comprised a 50%/50% split of trilobal rayon fibers having a 4.5 dtex and a spin finish of 0.06% and round rayon fibers having a 3.0 dtex and a 0.06% spin finish. Each of the fibers was 38 mm long. There were 7 layers in each of the Sample 11 samples where each of the layers had a basis weight of about 100 gsm plus/minus 7. The fibers were spunlaced.

Sample 12 comprised a 50%/50% split of trilobal rayon fibers having a 3.3 dtex and a spin finish of 0.12% and round rayon fibers having a 3.0 dtex and 0.06% spin finish. There were 7 layers in each of the Sample 12 samples where each of the layers had a basis weight of about 100 gsm plus/minus 7. The fibers were spunlaced.

Sample 13 comprised 100% trilobal rayon fibers having a 3.3 dtex and a spin finish of 0.06%. There were 7 layers in each of the Sample 13 samples where each of the layers had a basis weight of about 100 gsm. The fibers were spunlaced.

Data for the above samples were obtained using the Fluid Kinetic Test as described hereafter and the Dynamic Expansion test as described hereafter. The results of the testing are described in Table 3.

TABLE 3

|  | Middle Segment FKV 100 s-125 s | Minimal activation Dynamic Expansion Value @1 g below syngina range (super-8 g) TOP (mm) | Minimal activation Dynamic Expansion Value @1 g below syngina range (super-8 g) MID (mm) | Minimal activation Dynamic Expansion Value @1 g below syngina range (super-8 g) BOT (mm) | Average expansion (mm) |
|---|---|---|---|---|---|
| Sample 1 | 11.56 | 18.1 | 18.6 | 16.8 | 17.8 |
| Sample 2 | 9.28 | 17.7 | 18 | 18.3 | 18.0 |
| Sample 3 | 14.78 | 18.3 | 18.7 | 18.6 | 18.5 |

TABLE 3-continued

| | Middle Segment FKV 100 s-125 s | Minimal activation Dynamic Expansion Value @1 g below syngina range (super-8 g) TOP (mm) | Minimal activation Dynamic Expansion Value @1 g below syngina range (super-8 g) MID (mm) | Minimal activation Dynamic Expansion Value @1 g below syngina range (super-8 g) BOT (mm) | Average expansion (mm) |
|---|---|---|---|---|---|
| Sample 4 | 36.79 | 20.9 | 21.4 | 20.8 | 21.0 |
| Sample 5 | 15.22 | 20.1 | 20.7 | 20 | 20.3 |
| Sample 6 | 22.55 | 20.7 | 21.2 | 20.4 | 20.8 |
| Sample 7 | 11.33 | 20.1 | 20.5 | 19.8 | 20.1 |
| Sample 8 | 20.32 | 18.7 | 19.1 | 18.9 | 18.9 |
| Sample 9 | 17.58 | 20.5 | 20.8 | 20.3 | 20.5 |
| Sample 10 | 13.26 | 20.9 | 21.1 | 20.6 | 20.9 |
| Sample 11 | 18.54 | 19.9 | 20.2 | 19.9 | 20.0 |
| Sample 12 | 21.74 | 20.2 | 20.7 | 20.5 | 20.5 |
| Sample 13 | 37.09 | 20.6 | 21.0 | 20.2 | 20.6 |

Figure 8:
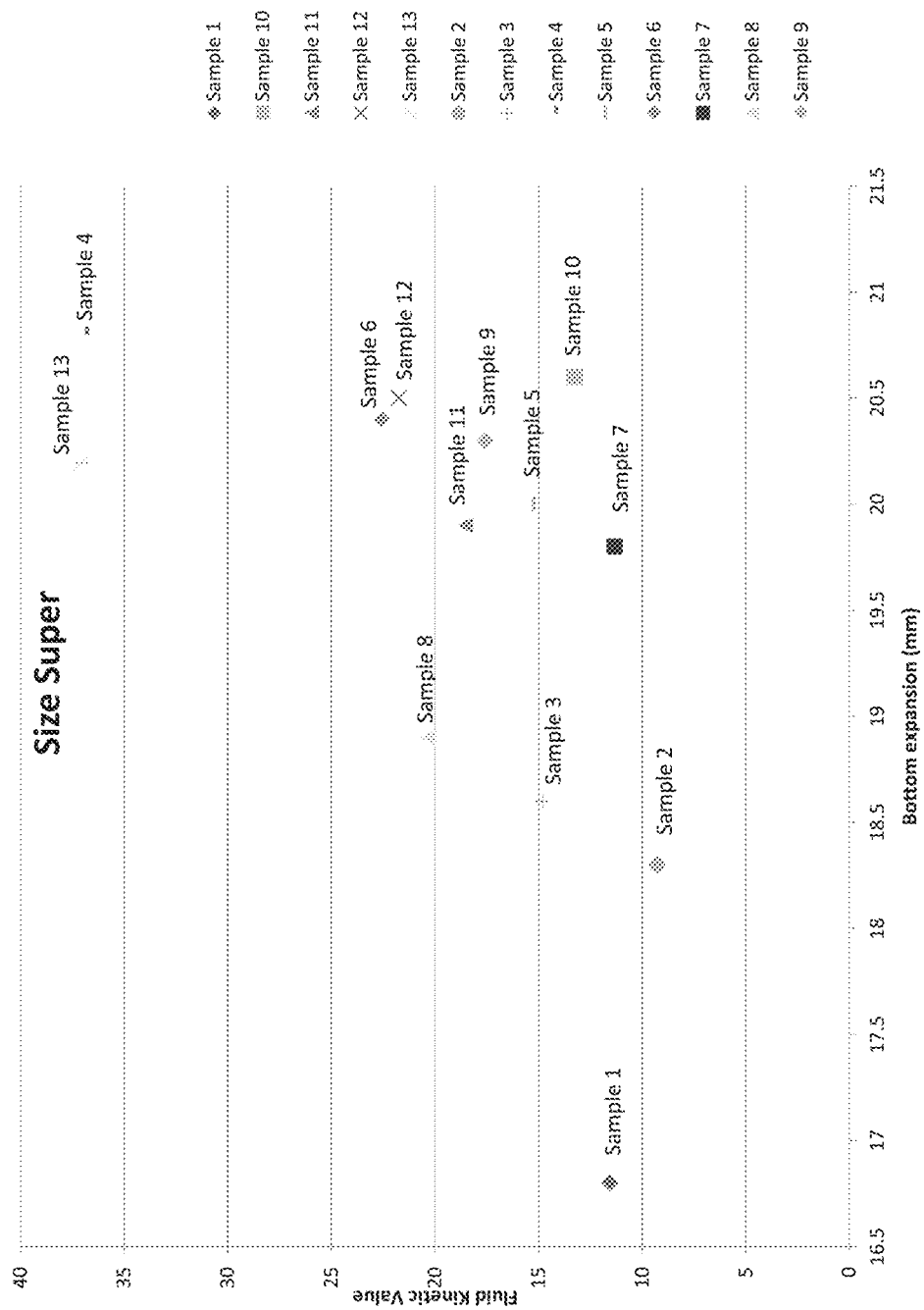
FIG. 8 is a graph depicting the FKV values and dynamic expansion data at the bottom of Samples 1-13.
Figure 9:
FIG. 9 is a graph depicting the FKV values and dynamic expansion data at the bottom of Samples 14-17.

As disclosed in Table 3, in some forms, Super-sized tampons of the present invention can exhibit a Fluid Kinetic Value ("FKV") of less than about 35 and an average expansion of at least 18.7 mm. In some forms, where the average expansion is at least 18.7 mm, the FKV may be less than about 30, less than about 25, less than about 20, less than about 15 less than about 10, less than about 5, greater than about 1, or any numbers within these ranges or any ranges created thereby. In some forms, where the FKV is less than 35, the average expansion can be greater than 19 mm, greater than 19.5 mm, greater than 20 mm, greater than 20.5 mm, greater than 21 mm, greater than 21.5 mm, greater than 22 mm, or any numbers within these ranges or any ranges created thereby. FIG. 8 is a graph visually depicting the fluid kinetic value versus the dynamic expansion value of each of the above Samples, i.e. 1-13 at the bottom of their respective tampons.

In some forms, the FKV may be less than about 35 while the dynamic expansion at the bottom of the tampon may be at least about 18.9 mm, at least about 19 mm or at least about 20 mm. In some forms, the FKV may be less than about 20 where the dynamic expansion at the bottom of the tampon may be at least about 19 mm or at least about 20 mm Additionally, Regular sized tampons were also tested. Descriptions of the samples tested are provided below.

Sample 14: Tampax® Pearl™, Regular;

Sample 15: Playtex™ Sport, Regular;

Sample 16 comprised a 50%/50% split of trilobal rayon fibers having a 3.3 dtex and round rayon fibers having a 3.0 dtex with a spin finish of 0.06%. Each of the fibers was 38 mm long. The fibers were spunlaced. There were 5 layers in each of the Sample 16 samples where each of the layers had a basis weight of about 100 gsm plus/minus 7. Each of the samples of Sample 16 were constructed to achieve a Syngyna absorption capacity in the Regular size range as disclosed herein.

Sample 17 comprised 100% trilobal rayon fibers having 3.3 dtex and a 0.12% spin finish. The fibers were spunlaced. The fibers had a length of 38 mm. There were 5 layers in each of the Sample 17 samples where each of the layers had a basis weight of about 100 gsm plus/minus 7. Each of the samples of Sample 17 were constructed to achieve a Syngyna absorption capacity in the Regular size range as disclosed herein.

Data for the above samples were obtained using the Fluid Kinetic Test as described hereafter and the Dynamic Expansion test as described hereafter. The results of the testing are described in Table 4.

TABLE 4

| | Middle Segment FKV 100 s-125 s | Minimal activation Dynamic Expansion Value @1 g below syngina range (super- 5 g) TOP (mm) | Minimal activation Dynamic Expansion Value @1 g below syngina range (super- 5 g) MID (mm) | Minimal activation Dynamic Expansion Value @1 g below syngina range (super- 5 g) BOT (mm) | Average expansion (mm) |
|---|---|---|---|---|---|
| Sample 14 | 11.40 | 18.45 | 18.71 | 17.32 | 18.2 |
| Sample 15 | 6.90 | 15.99 | 16.6 | 14.97 | 15.9 |
| Sample 16 | 6.70 | 17.77 | 17.9 | 16.31 | 17.3 |
| Sample 17 | 9.10 | 18.01 | 18.17 | 16.72 | 17.6 |

As disclosed in Table 4, in some forms, Regular-sized tampons of the present invention can exhibit a Fluid Kinetic Value ("FKV") of less than about 10 and an average expansion of at least 17 mm. In some forms, where the average expansion may be in a range from about 16 mm to about 19 mm and the corresponding FKV may be less than about 10, less than about 9.5, less than about 8, less than about 7 or any numbers within these ranges or any ranges created thereby.

Method of Making

Referring back to FIGS. 1A-1C, the tampons of the present disclosure can generally be manufactured by conventional manufacturing techniques known in the art with the exception of the production of the absorbent material. As noted above, the absorbent material should have sufficient Z-direction integration of the fibers so that fluid insults can transfer along the length of the pledget 10 (shown in FIGS. 1A-1C) as well as along the width 150 and thickness T.

For needle punching, some basic equipment is needed to produce the web. For example, bale openers, a mixer, carding machines, a preneedler and a needle loom. The formation of the nonwoven webs prior to needle punching is conventional. For the needle punching the preneedler used was a Truzschler ENL-01, ID #364600, 5000 needles per meter, 15×16×36×3.5 M222 G 53017 needles available from Trutzschler. And, the needle loom was an Asselin Model A50RL, series 1189, 7000 needles per meter, with 15×32×40×3.5 R222 G530P7 needles available from Andritz.

For spunlacing, some basic equipment is needed to produce the web. For example, bale openers and carding machines. The formation of the nonwoven webs prior to the spunlacing operation is conventional. For the spunlacing operation, an Aqua-Jet spunlace system from Fleissner, a dryer from Trutzschler, a drum dryer from Fleissner, and a winder from Menzel was utilized. The number of jet heads was Pre Wet+2 having a plurality of holes each having a diameter of 120 μm and the number of holes being 40 holes per inch. The sleeve type was MPS, and the pressures used were 20, 40, and 50 bar.

Figure 10A:
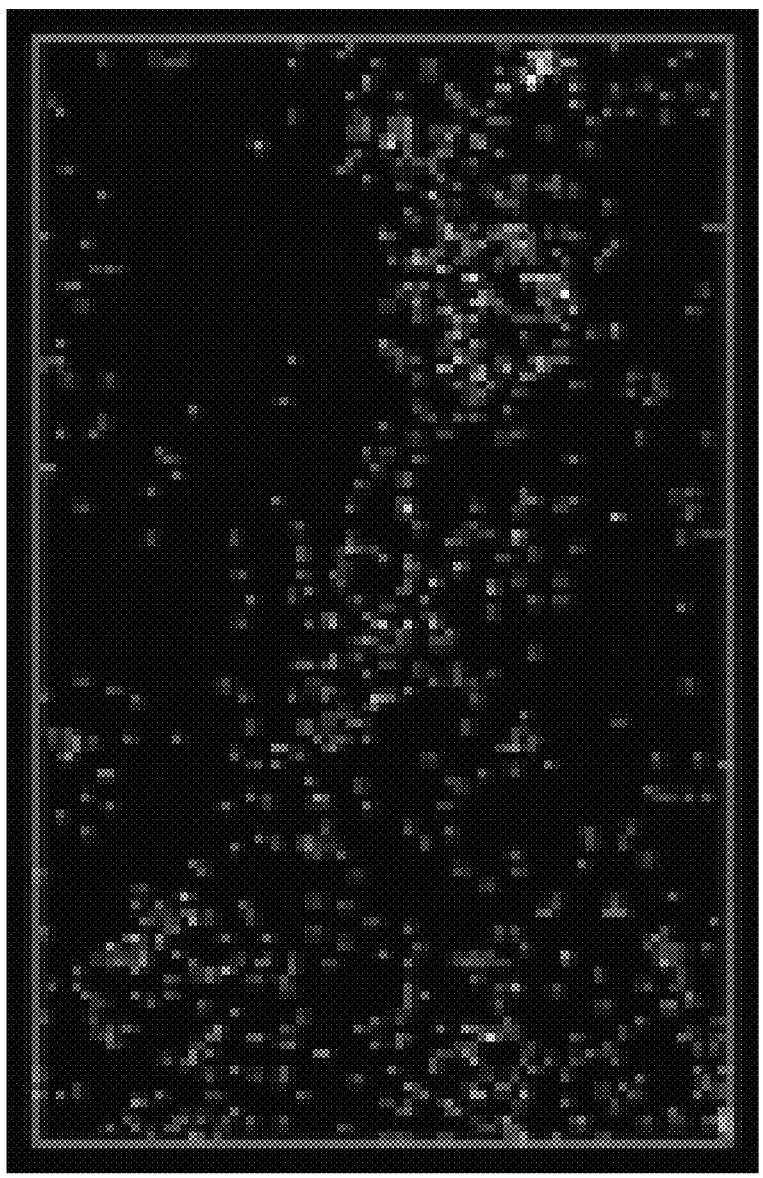
FIGS. 10A-10C are microCT projections of scans which show relative average length of Z-oriented fibers in a primary absorbent member with carded and calendared fibers.
Figure 10B:
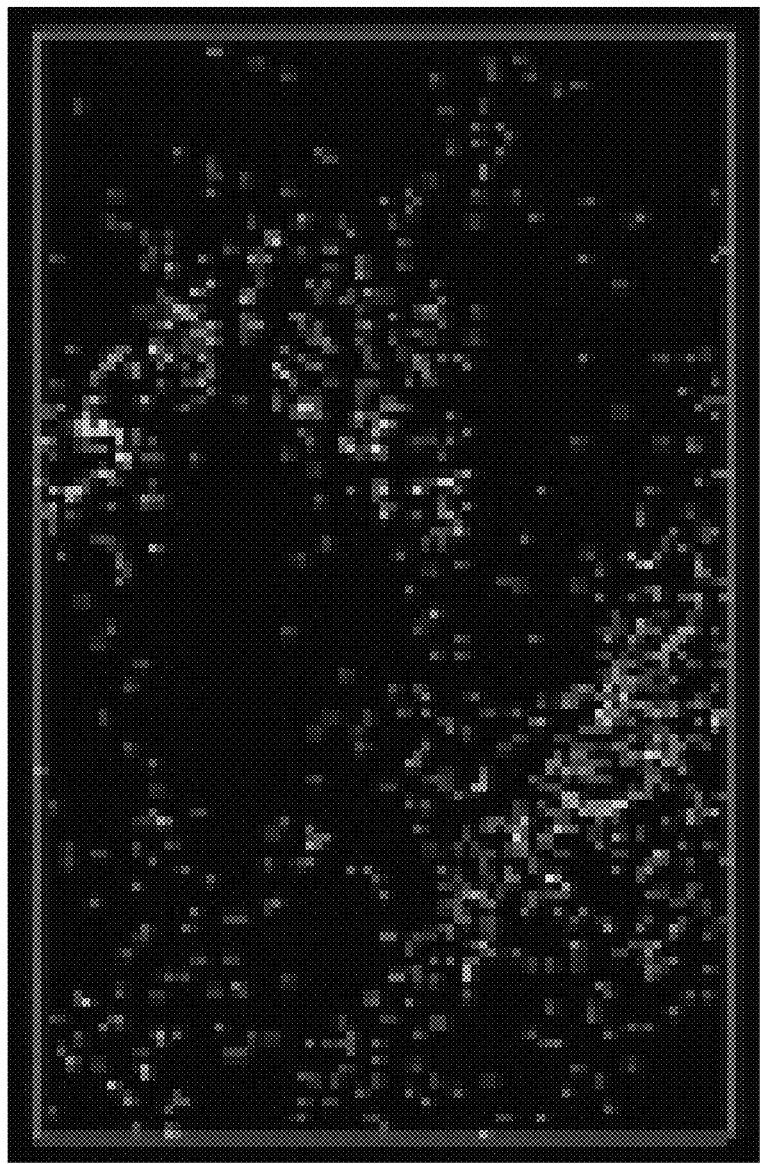
Figure 10C:
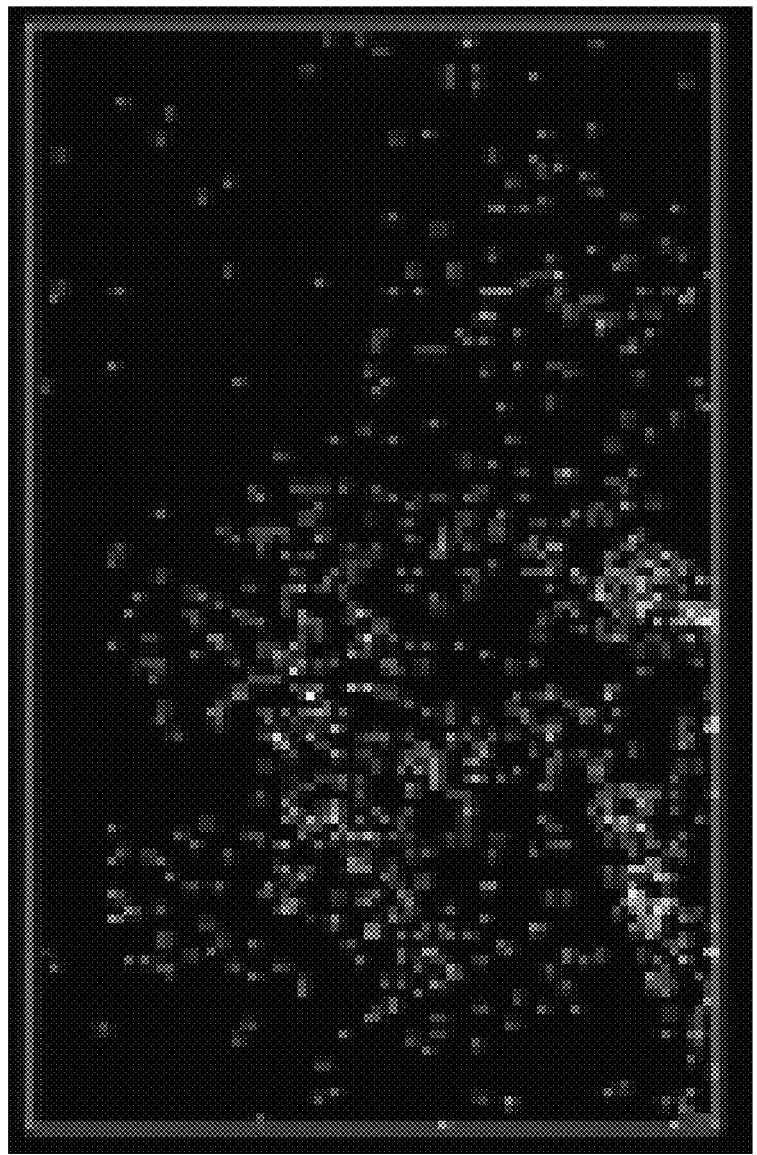
Figure 11A:
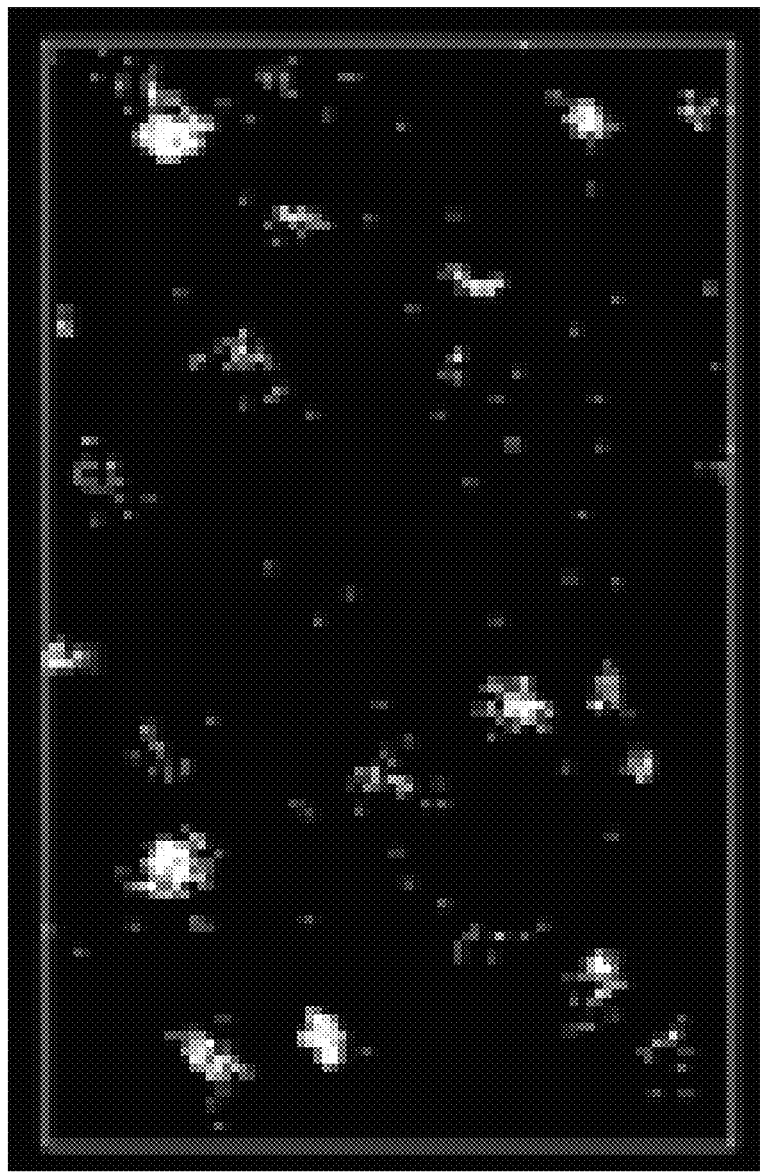
FIGS. 11A-11C are microCT projections of scans which show relative average length of Z-oriented fibers in a needlepunched primary absorbent member (code B). in accordance with the present disclosure.
Figure 11B:
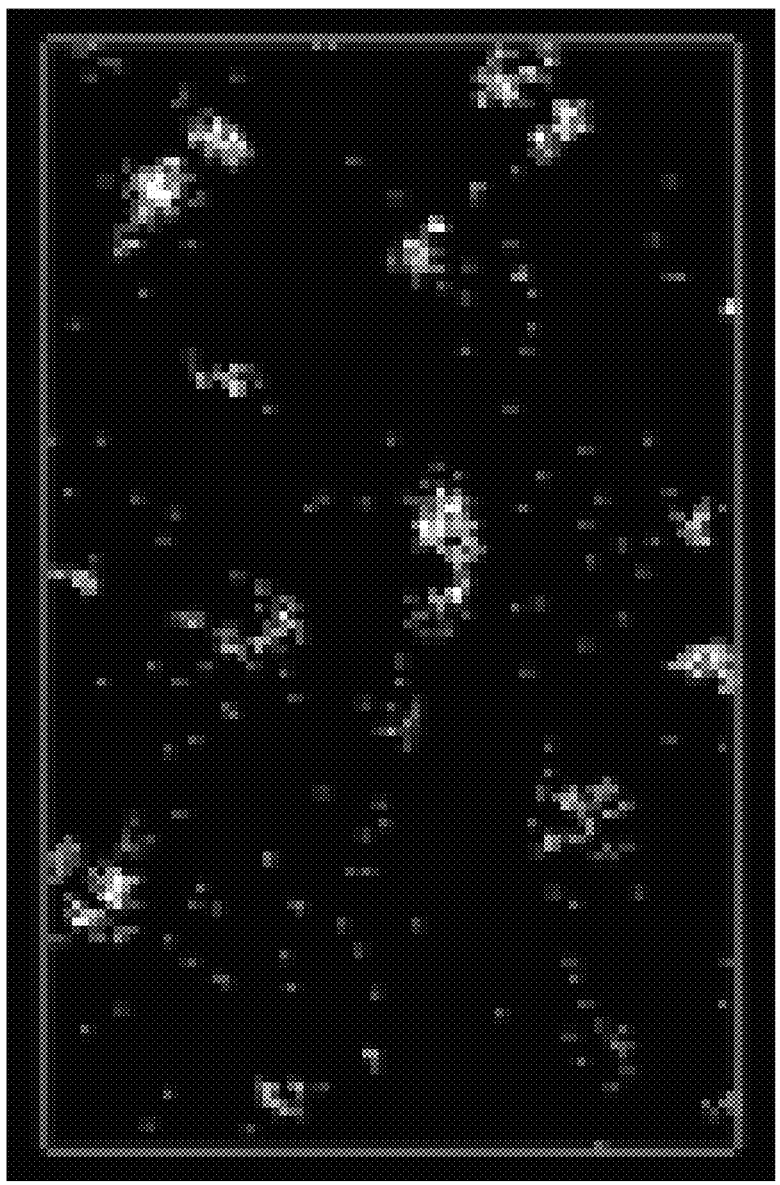
Figure 11C:
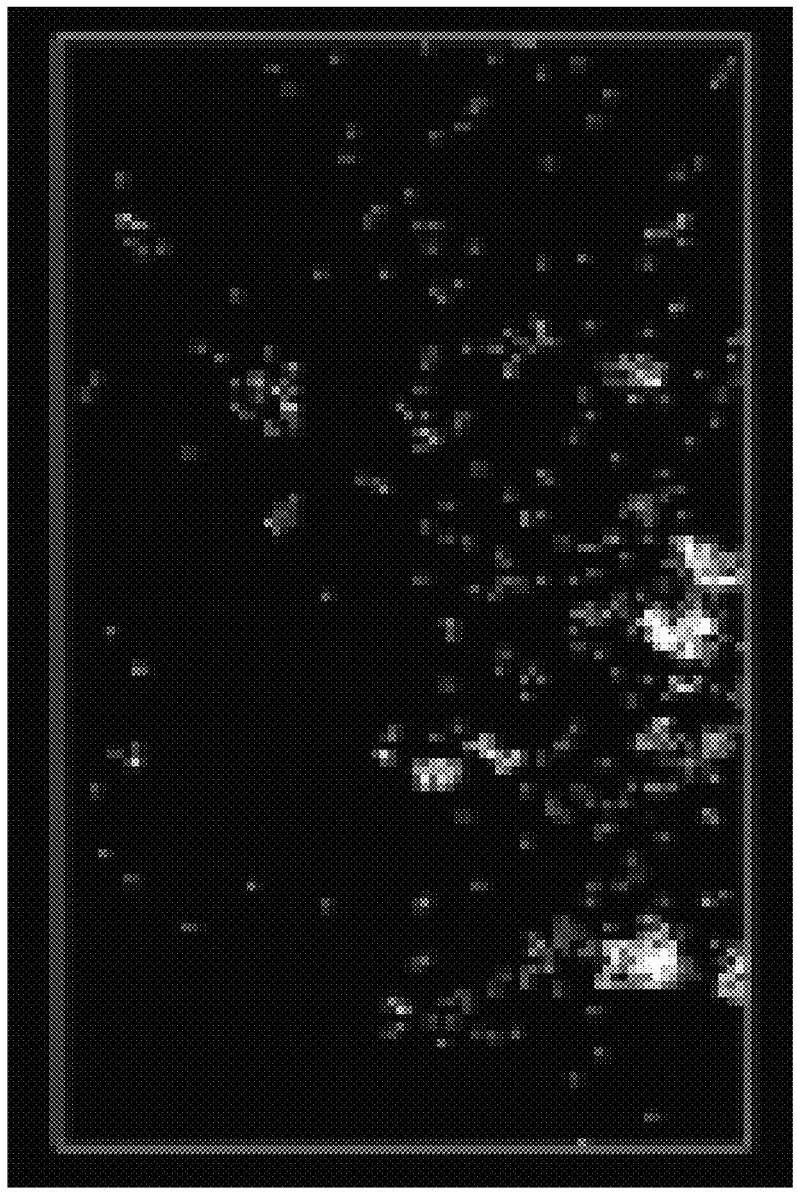
Figure 12A:
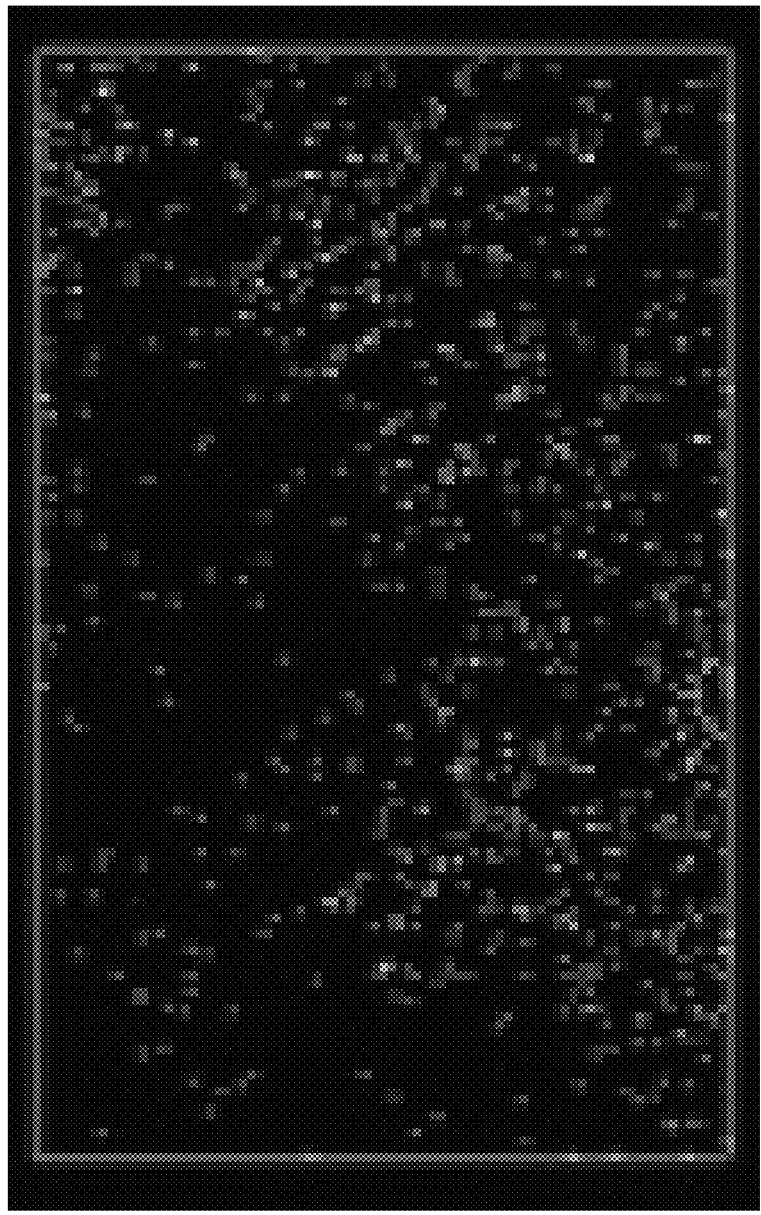
FIGS. 12A-12C are microCT projections of scans which show relative average length of Z-oriented fibers in a primary absorbent member with carded and calendared fibers.
Figure 12B:
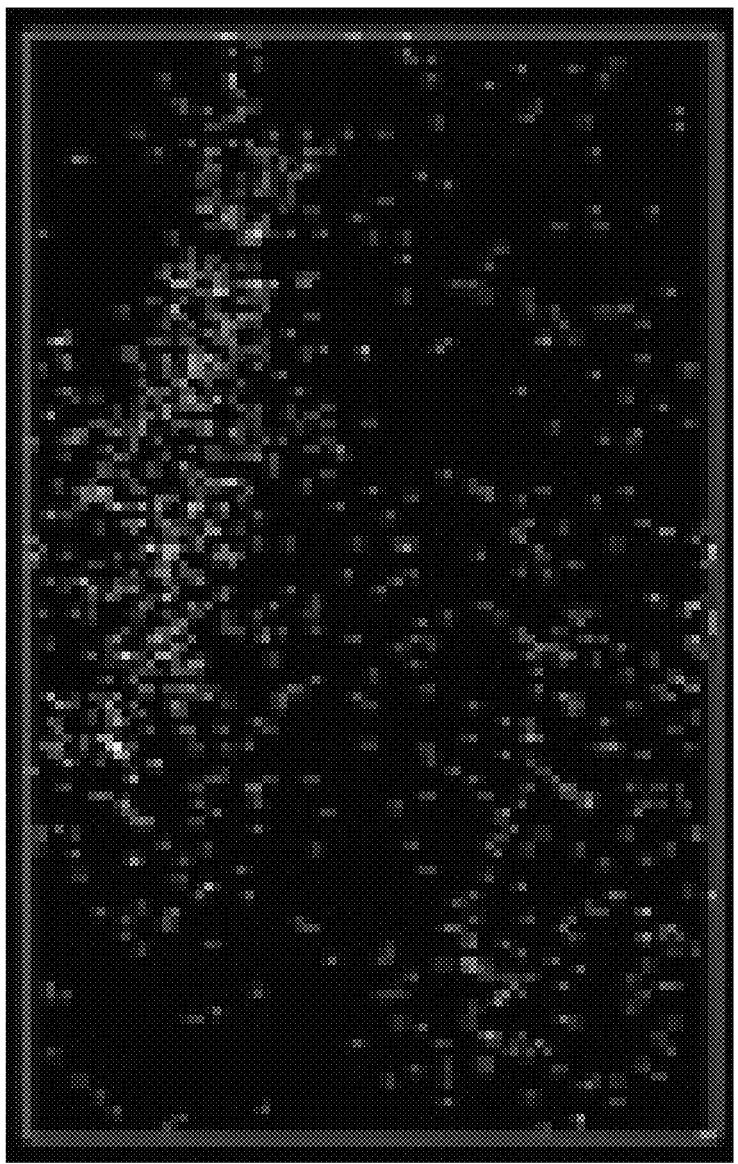
Figure 12C:
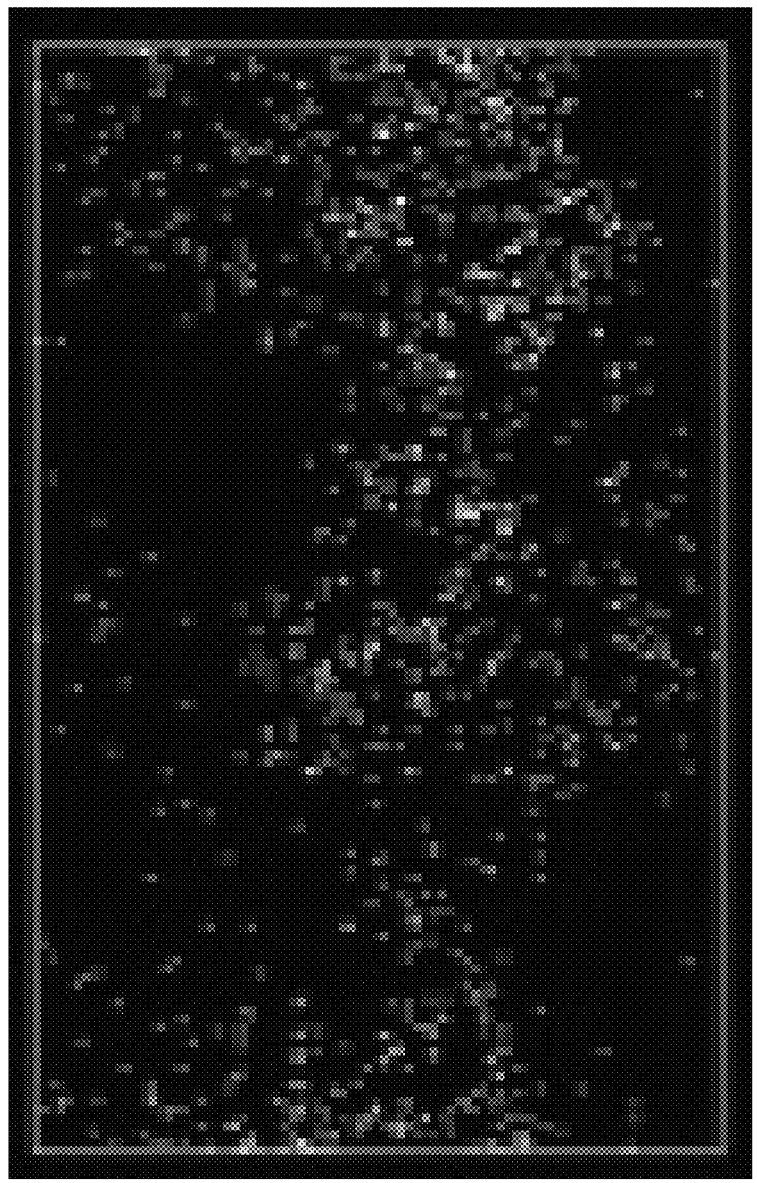
Figure 13A:
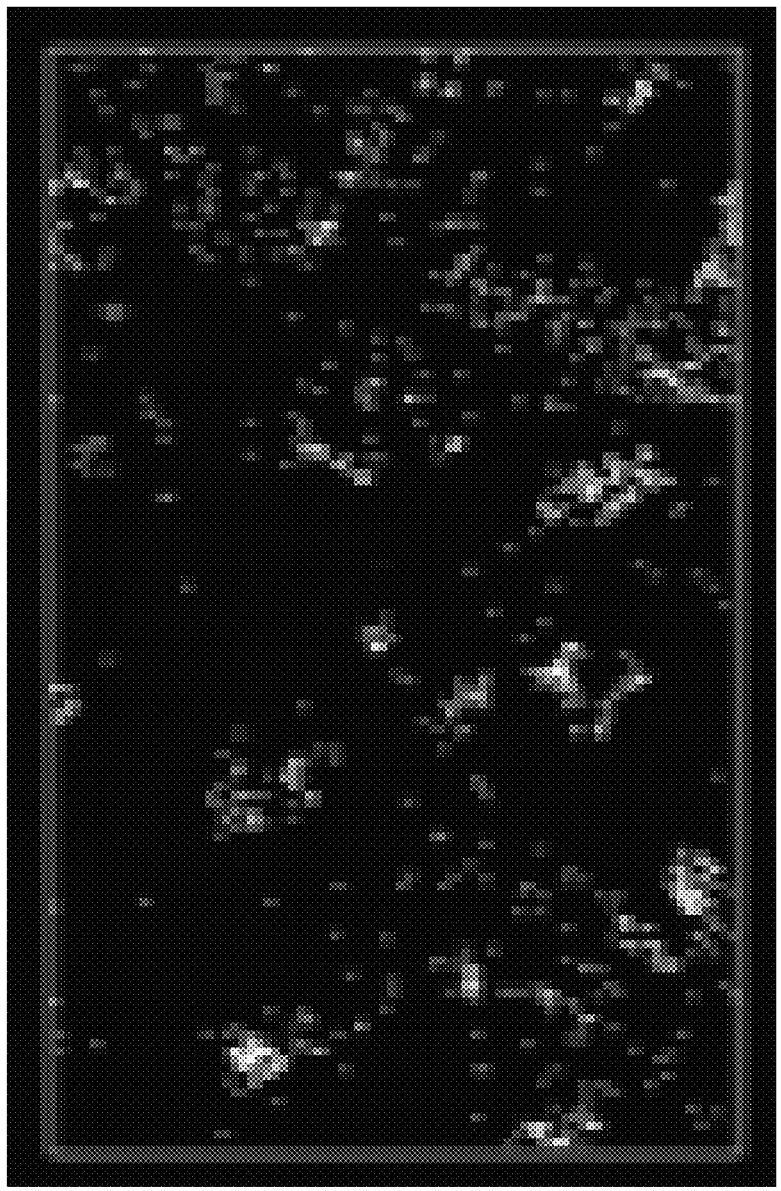
FIGS. 13A-13C are microCT projections of scans which show relative average length of Z-oriented fibers in a primary absorbent member of commercially available product.
Figure 13B:
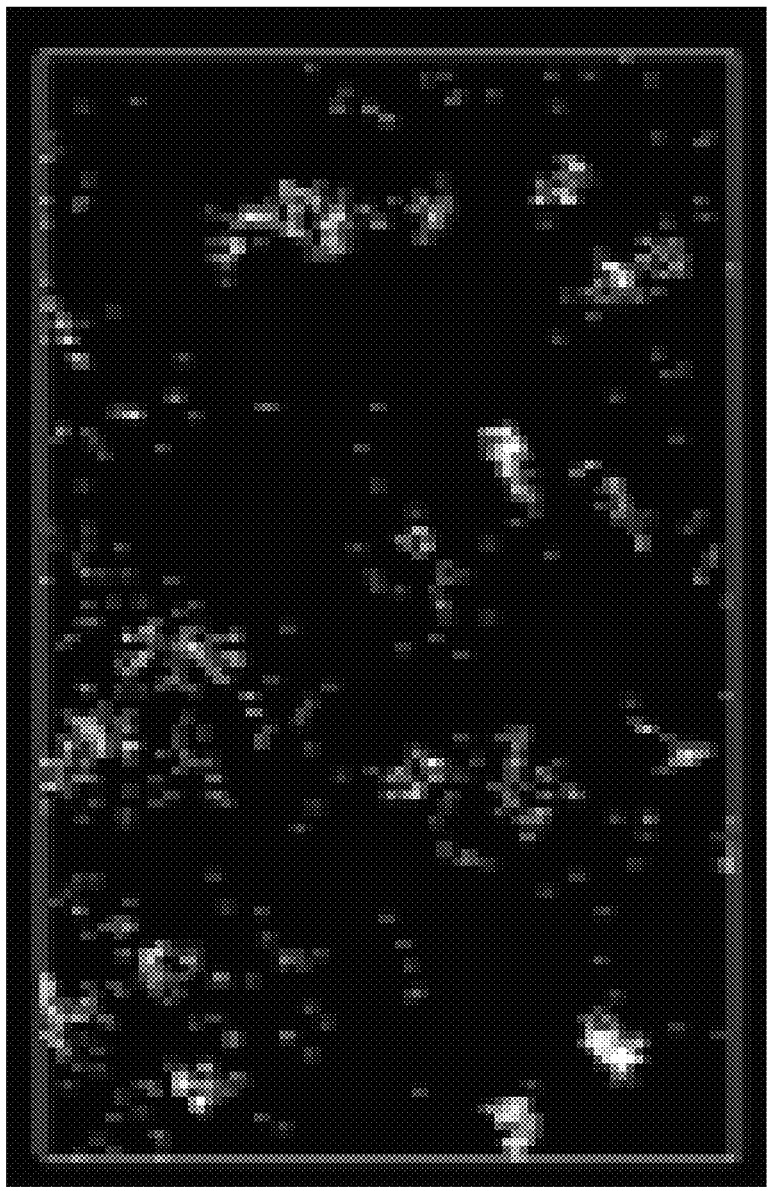
Figure 13C:
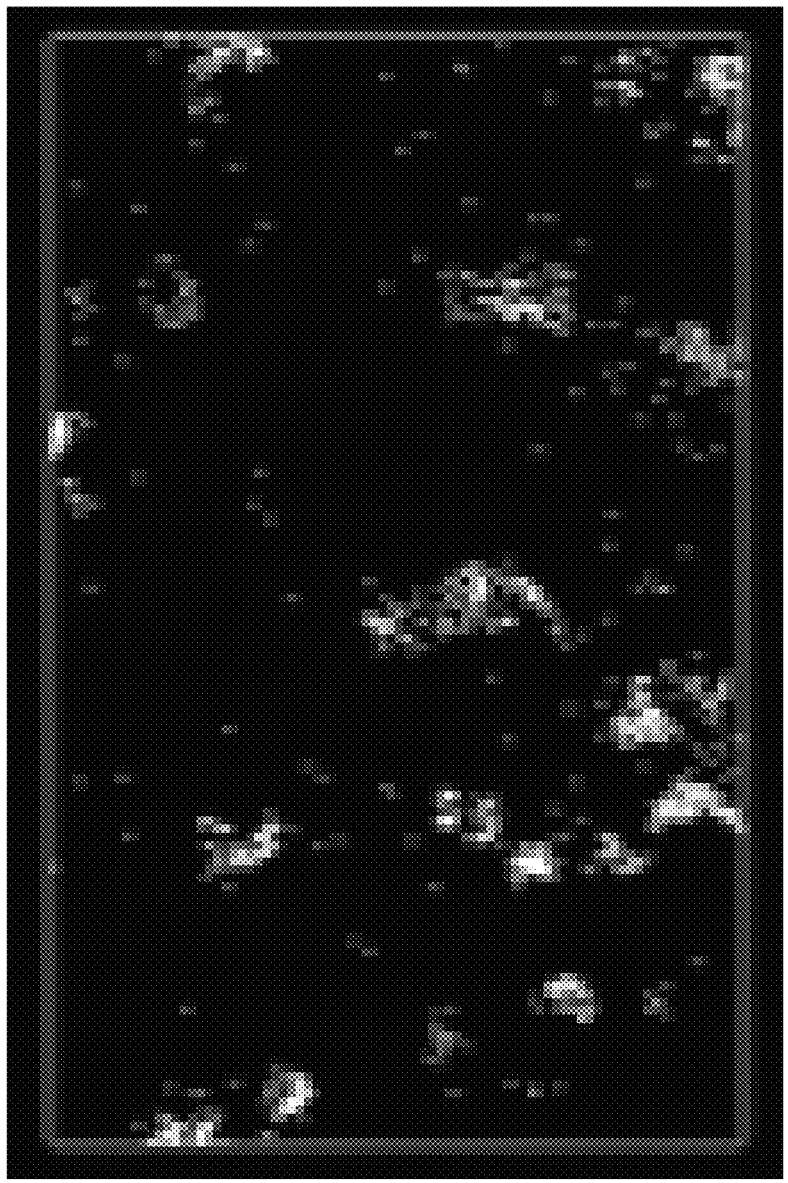

FIGS. 10A-13C show the results of the Z-cluster test. FIGS. 10A-10C are depictions of a carded, calendared, primary absorbent member comprising 75 percent Galaxy™ rayon and 25 percent cotton, having a basis weight of about 562 gsm. FIGS. 11A-11C are depictions of a needlepunched primary absorbent member having a fiber blend ratio of 75 percent Galaxy™ rayon and 25 percent cotton, having a basis weight of about 553 gsm constructed in accordance with the present disclosure. FIGS. 12A-12C are depictions of a carded, calendared, primary absorbent member comprising 100 percent Galaxy™ rayon having a basis weight of about 535 gsm. FIGS. 13A-13C are depictions of a primary absorbent of a commercially available tampon, sold under the trade name Walgreens™ Perfection Silk™ Regular. The data provided in Table 1 shows the differences between the various samples tested. Specifically, Configuration 1 is applicable to FIGS. 10A-10C; Configuration 2 is applicable to FIGS. 11A-11C; Configuration 3 is applicable to FIGS. 12A-12C; and Configuration 4 is applicable to FIGS. 13A-13C.

Test Methods:
Dynamic Expansion

Expanded Width is measured from the change in diameter of a tampon under pressure as test fluid is introduced at a specified flow rate. The expansion at three sites along the length of the tampon is measured at a specified fluid capacity and averaged to give the Expanded Width to the nearest 0.01 mm.

Figure 3:
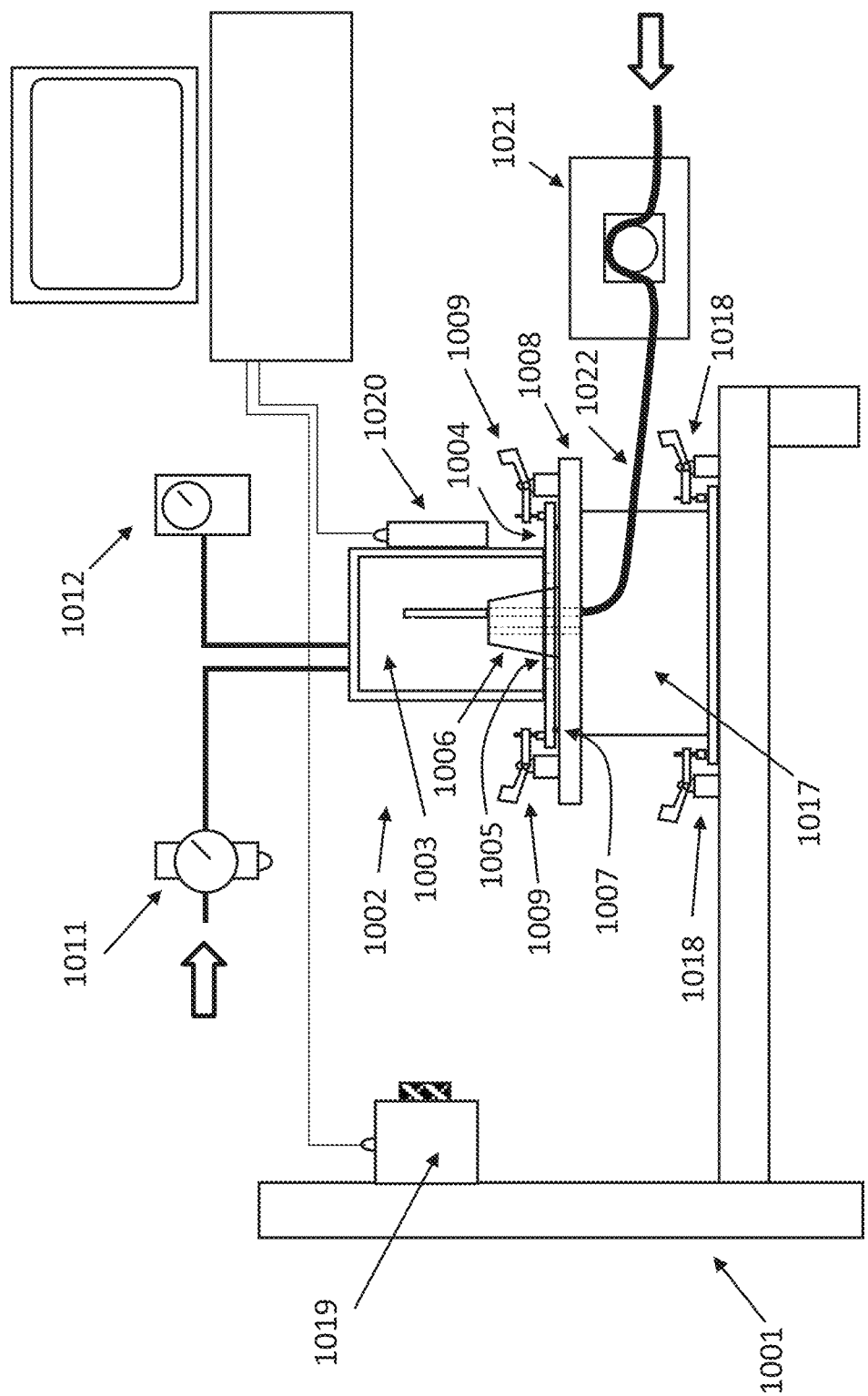
FIG. 3 is a schematic diagram showing an apparatus for measuring the dynamic expansion of tampons.
Figure 4:
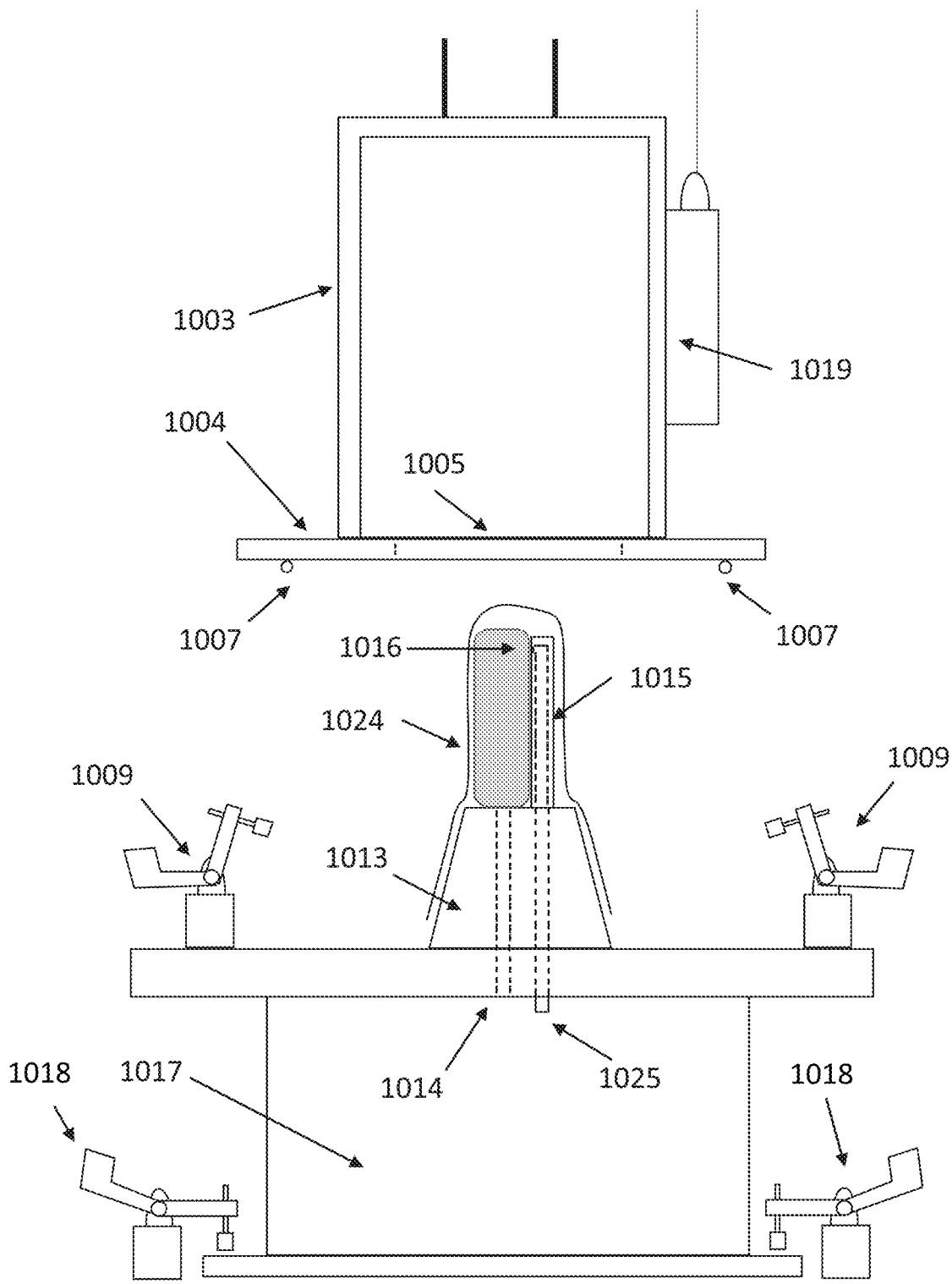
FIG. 4 is a schematic diagram of the apparatus of FIG. 3 with some of the features of FIG. 3 removed for ease of visualization.

Referring to FIGS. 3 and FIG. 4, the test apparatus includes a frame 1001 that supports the expansion assembly 1002. The assembly is constructed of a pressurized Plexiglas chamber 1003 with a bottom plate 1004. The plate has a circular opening 1005 such that the tampon mounting base 1006 can be inserted through the opening. The bottom plate also has a silicone gasket 1007 that surrounds the opening 1005 and is used to seal the chamber 1003 against the mounting platform 1008 using clamps 1009. The chamber is pressurized to 3.45 kPa using a compressed air source not shown). The chamber pressure is adjusted via a pressure regulator 1011 and calibrated manometer 1012 (standardized to ANSI standards).

The tampon mounting base 1006 is fixed to the mount plate 1008 and is made up of a tapered cylindrical base 1013 with a 3 mm diameter drain hole 1014 that extends from the top of the base and through the mount plate. A Plexiglas delivery tube 1015 (9.5 mm O.D by 3 mm I.D.) extends 48.5 mm above base 1013. The fluid path originates from a tube connector 1025 below the mount plate 1008 and extends through the mount base and terminates in a 1.5 mm opening 1016 on the side of the delivery tube 1015 (the top of the tube is sealed). The opening is 5 mm down from the top of the tube and faces the tampon. The mounting platform 1008 has a base 1017 that is open on two of its sides (to allow cleaning of fluid that drains from the drain hole 1014) and clamps 1018 to the frame 1001.

The imaging system consist of a sensor/camera 1019 (gray scale, minimum of 640×480 pixels, such as the Cognex DVT 545, available from PDF Supply, Cary N.C., or equivalent) and is attached to the frame 1001 and light box 1020 (such as the Cognex DVT Smart Light, also available from PDF Supply, Cary N.C., or equivalent) for backlighting is attached to the pressure chamber 1003. The camera is adjusted such that the total length of the sample is contained in the field of view. The system collects images and adjusts the threshold such that the sample in the foreground is dark against a light background. The digital images are analyzed using software suitable for making calibrated linear measurements. The software is calibrated for linear dimensions to the nearest 0.01 mm using standard cylinders of known diameters ranging from 12 to 24 mm. The horizontal width of the sample is measured at three sites; the "top" at 28% of the tampon length, "middle" at 50% of the tampon length, and "bottom" at 67% of the tampon length. All positions measured from the top of the tampon.

The test fluid used is Defibrinated Sheep's Blood, minimum 38% packed cell volume (available at Cleveland Scientific Ltd., Bath, Ohio, or equivalent). The test fluid is placed in a 250 mL reservoir and continuously and moderately stirred to avoid separation. The fluid is maintained at 23° C. ±3 C.° during use. The test fluid is supplied from the reservoir to the delivery tube 1015 with peristaltic pump tubing 1022. A peristaltic pump 1021 (such as Master Flex, available from Cole Parmer, Verner Hills, Ill., or equivalent) delivers the test fluid at 1.0 g/min ±0.02 g/min. The peristaltic pump tubing and delivery tube are filled before the start of testing.

Samples still in their applicators and wrappers are conditioned 23° C.±3° C. and 50±5% relative humidity for 4 hours prior to testing. Samples are not removed from their wrappers or applicators until immediately prior to testing. Remove the tampon from its applicator and cut the withdrawal string at the base of the tampon. If a braid or skirt is present on the tampon, it is left intact. Measure the dry mass of the tampon to the nearest 0.01 gram. Using a digital Vernier caliper (e.g. Digimatic 500 series, Mitutoyo, or equivalent) measure the maximum length (not including skirt or braid if present) and maximum width and record each to the nearest 0.01 mm. This width is the Tampon Dry Width.

Place a small piece of 2-sided tape onto the sample side of the delivery tube 1015 making sure not to cover the side opening 1016. If the tampon's construction is a compressed, flat, sewn pad, mount the tampon so that the sewn side seam is toward the fluid delivery tube. For other constructions, direct any seam, if present, toward the delivery tube. Mount the sample onto the delivery tube with the top of the sample extending 2 mm above the top of the tube. If the sample length is greater than the height of the delivery tube, align the bottom of the sample to the top of the mounting base 1006. If the sample contains a braid or skirt, allow that structure to drape down the mounting base (opposite the delivery tube), assuring that it does not protrude past the width of the sample.

Unroll an unlubricated condom 1024 (condom compiling to ASTM 3492) and place loosely over the sample, delivery tube and upper portion of mounting base 1006 such that the end extends approximately 2 cm above the top of the sample. Place the expansion assembly over the sample and mounting base and clamp in place. Turn on the compressed air and adjust the pressure in the assembly to 3.45 kPa as read by the manometer. The condom should now be snug against the tampon. Start the vision system and inspect the resulting image. If folds of the condom appear at the sides or on top of sample in image, open chamber, readjust the condom, and repeat this step until the condom is smooth along the sides of the tampon in the image, e.g., no creases/wrinkles are visible.

Program the imaging system to take an image every 5 sec. Start the program and peristaltic pump. Continue flow to the sample until test fluid is detected at the bottom of the drain tube 1014. With the calibrated image software measure the width of the at the "top", "middle" and "bottom" sites for all images taken and record to the nearest 0.01 mm. Calculate the Corrected Widths as:

Corrected Width$_{[s,i]}$=Dry Tampon Width+Width$_{(s,i)}$−Width$_{[s,0]}$

Where s=site (Top, Middle, or Bottom); i=time (in sec); all widths in mm

From these values, separate curves for the Corrected Width (mm) vs Time (sec) can be constructed for each measured site.

Expanded Width is defined as the Corrected Width at a size-specific test mass. For each tampon select the Test Time for the appropriate absorbency term from Table 5. From each of the site Corrected Width vs Time curves read and record the Corrected Width for the "Top", "Middle" and "Bottom" sites at that selected Test Time. Calculate the arithmetic average of the three values and report as the Expanded Width to the nearest 0.01 mm.

In like fashion analyze 6 replicate samples, calculate the arithmetic average and report as the Expanded Width to the nearest 0.01 mm.

TABLE 5

| Absorbency Term | Absorbency Range (g) | Test Mass (g) | Test Time (s) |
| --- | --- | --- | --- |
| Light absorbency | 6 and under | 3.0 | 180 |
| Regular absorbency | 6 to 9 | 5.0 | 300 |
| Super absorbency | 9 to 12 | 8.0 | 480 |
| Super Plus absorbency | 12 to 15 | 11.0 | 660 |

TABLE 5-continued

| Absorbency Term | Absorbency Range (g) | Test Mass (g) | Test Time (s) |
| --- | --- | --- | --- |
| Ultra absorbency | 15 to 18 | 14.0 | 840 |
| No term | 18 and above | 17.0 | 1020 |

Fluid Kinetics Testing

Figure 5:
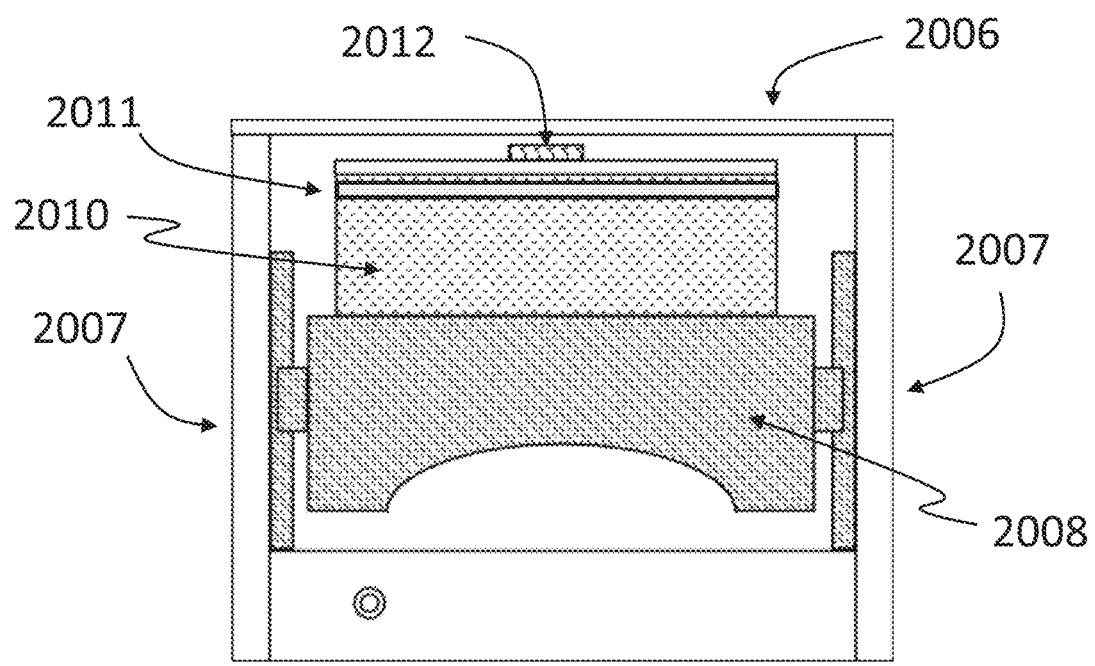
FIG. 5 is a schematic diagram of an NMR-MOUSE apparatus.

The NMR-MOUSE (Mobile Universal Surface Explorer) is a portable open NMR sensor equipped with a permanent magnet geometry that generates a highly uniform gradient perpendicular to the scanner surface. Referring to FIG. 5, a frame 2007 with horizontal plane 2006 supports the specimen and remains stationary during the test. A flat sensitive volume of the specimen is excited and detected by a surface rf coil 2012 placed on top of the magnet 2010 at a position that defines the maximum penetration depth into the specimen. By repositioning the sensitive slice across the specimen by means of a high precision lift 2008, the scanner can produce one-dimensional profiles of the specimen's structure with high spatial resolution.

An exemplary instrument is the Profile NMR-MOUSE model PM25 with High-Precision Lift available from Magritek Inc., San Diego, Calif. Requirements for the NMR-MOUSE are a 100 µm resolution in the z-direction, a measuring frequency of 13.5 MHz, a maximum measuring depth of 25 mm, a static gradient of 8 T/m, and a sensitive volume (x-y dimension) of 40 by 40 mm$^2$. Before the instrument can be used, perform phasing adjustment, check resonance frequency and check external noise level as per the manufacturer's instruction. A syringe pump capable of delivering test fluid in the range of 1 mL/min to 5 mL/min±0.01 mL/min is used to dose the specimen. All measurements are conducted in a room controlled at 23° C.±0.5° C. and 50%±2% relative humidity.

The test solution is Paper Industry Fluid (PIF) prepared as 15 g carboxymethylcellulose, 10 g NaCl, 4 g NaHCO$_3$, 80 g glycerol (all available from SigmaAldrich) in 1000 g distilled water. Two (2) mM/L of Diethylenetriaminepentaacetic acid gadolinium (III) dihydrogen salt (available from SigmaAldrich) is added to each. After addition the solutions are stirred using an orbital shaker at 160 rpm for one hour. Afterwards the solutions are checked to assure no visible undissolved crystals remain. The solution is prepared 10 hours prior to use.

Figure 6:
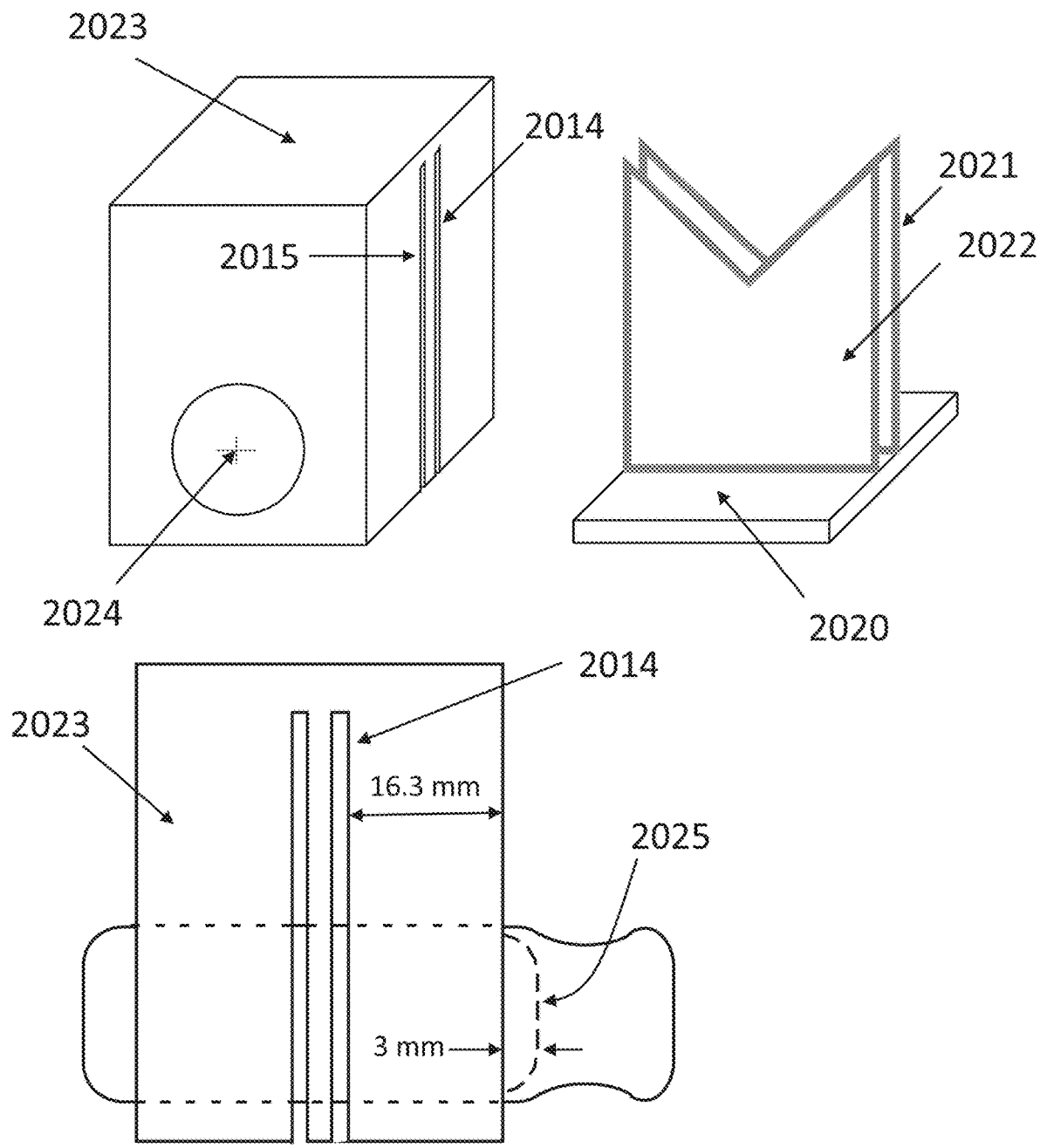
FIG. 6 is a schematic diagram showing an apparatus for creating samples for the apparatus of FIG. 5.

The guillotine sample cutter is shown in FIG. 6. A platform 2020 approximately 12 mm thick with two embedded notched blades 2021 and 2022. The blade extends 39 mm above the platform, by 38 mm wide with a notch that's center is at 23 mm above the platform. The blade is approximately 0.70 mm thick and has been sharpened to a knife-edge on the contact edges within the notch. The sample holder 2023 is made of a Delrin block, 48 mm tall by 38 mm deep by 38 mm wide. A hole 2024, 16.5 mm in diameter is drilled through the depth of the block. Observed from the front, the hole is centered 12.3 mm from the bottom edge of the block and is centered in the width dimension. If necessary, the hole can be enlarged to accommodate larger diameter tampon applicators. The holder 2023 has two vertical slots 2014 and 2015 cut into the entire width of the holder, origination at the bottom and terminating 8 mm from the top of the holder. They are width and spacing are such that the blades 2021 and 2022 can fit into them. The back vertical slot 2014 is 16.3 mm from the back of the block. The slots and blades are spaced such that the resulting cut sample is 6.0 mm long For the Kinetic Experiment, program the NMR-MOUSE for a CPMG pulse sequence using the following conditions:
Measurement Depth=5 mm
Repetition Time=200 ms
90° Amplitude=−7 dB
180° Amplitude=0 dB
Pulse Length=5 μs Echo Time=90 μs
Number of Echoes=128
Echo Shift=1 μs
Experiments before trigger=50
Experiments after trigger=2000
Rx Gain=31 dB
Acquisition Time=8 μs
Number of Scans=1

Rx Phase is determined during the phase adjustment as described by the vendor. A value of 230° was typical for our experiments. Pulse length depends on measurement depth which here is 5 mm. If necessary the depth can be adjusted using the spacer 2011.

Calibration of the signal amplitude is performed using 200 μm thick filter paper (Whatman 1004-125 Grade 4 Qualitative Filter Paper, No. 1004-125, or equivalent) which are cut into 3.0 cm×3.0 cm squares. Signal amplitude is tested at loadings of 0 μL, 20 μL, 60 μL, 80 μL, 160 μL. Place a 40 mm×40 mm×1 mm glass slide on the NMR-MOUSE, then the filter paper square. Using a calibrated Eppendorf Pipettor, accurately pipet the dose onto the filter paper and allow it to soak in for 30 sec. Add a second 40 mm×40 mm×1 mm glass slide on top of the filter paper. Using the precision lift adjust the height of the specimen so that the desired target region is aligned with the instruments sensitive volume. Take 500 measurements. In like fashion collect data for each of the loadings. Calculate the average of signal amplitudes for each load and construct a calibration curve of Volume (μL) versus Signal using least squares linear regression. Calculate the slope and y-intercept and record to 5 significant figures.

Samples are conditioned 23° C. ±3 C.° and 50±5% relative humidity for 4 hours prior to testing. Remove the plunger from its applicator. Using the draw string pull the tampon to the back of the applicator. Insert the applicator with tampon into the sample holder 1023 2023. Align the back of the tampon 2025 three mm outside of the sample holder. Place the holder with sample onto the guillotine blades and press the holder down onto the blades. Remove the cut specimen and assure that there was a clean perpendicular cut. If not, prepare another specimen.

Prepare a sandwich of two 40 mm×40 mm by 0.1 mm glass slides, held together with a 30 mm×30 mm×0.3 mm piece of 2-sided tape. The total thickness should be 500 μm thick. Place the tampon specimen that was cut in 6 mm thick in the previous step onto the NMR-MOUSE. Insertion end side of the cut specimen faces top. The sandwich of the glass slides is placed on top of the specimen. Using the precision lift adjust the height of the specimen so that the desired target region is aligned with the instruments sensitive volume. For this experiment the target is 1000 μm from the bottom of the specimen. Program the syringe pump to deliver 1.00 mL/min±0.01 mL test fluid for 0.4 min. Start the measurement and collect NMR Amplitude (a.u.) for 16.5 sec before initiating fluid flow to provide a signal baseline. Position the outlet tube from the syringe pump over the center of the specimen. Remove the glass slides and dispense the test fluid onto the tampon specimen. As soon as the test fluid is applied to the specimen, place the glass slides back on the top of the specimen. Continue collection of NMR amplitude data during fluid introduction up to 200 sec.

Figure 7:
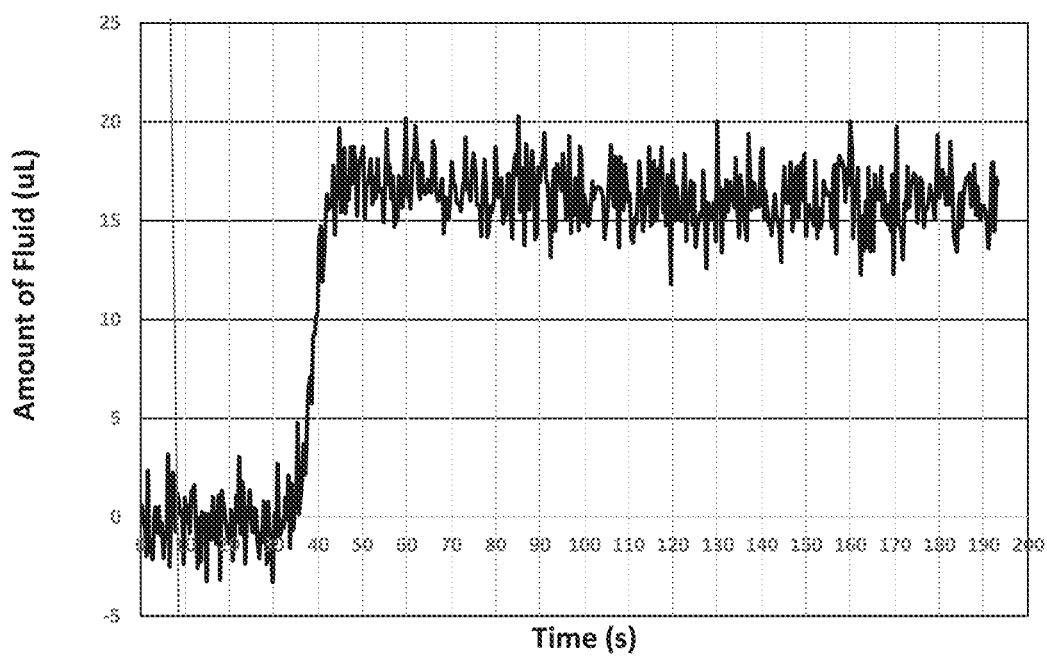
FIG. 7 is an exemplary plot from the apparatus of FIG. 5.

Using the calibration curves slope and y-intercept, calculate and plot a Volume (μL) verses Time (s) plot. A representative plot is given in FIG. 7. From the plot calculate an average volume in the target zone using the values from 100 sec to 125 sec. Record average to the nearest 0.01 μL.

In like fashion analyze two more replicate samples. Calculate the average of the three analyses and report to the nearest 0.01 μL. This value is the FKV—Fluid Kinetic Value.

Tampon Density

The following steps are followed to calculate the density of a tampon according to the present invention. The tampon withdrawal string (or comparable withdrawal structure) and any existing secondary absorbent feature (e.g., a braid) is cut at the bottom of the tampon absorbent body. The tampon body is then weighed to the nearest 0.01 grams. And the tampon body length is measured to the nearest 0.1 millimeters. The tampon body is then immerse into isopropyl alcohol for 30 seconds or until air bubbles stop. Remove the tampon from the alcohol and allow the excess alcohol to drip from the tampon for 15 seconds. Separately a test cylinder with spout is filled with isopropyl alcohol until it overflows at the spout into a 50 milliliter beaker. Tare the 50 milliliter beaker. Place the tampon body after the excess has dripped from the same slowly into the cylinder containing the standard volume of isopropyl alcohol. Collect the overflow of isopropyl alcohol from the spout that resulted from the addition of the tampon body. Obtain the weight of the isopropyl alcohol that overflowed the test cylinder to the nearest 0.01 grams.

Tampon volume (milliliters)=weight of overflowed alcohol/0.780 grams per milliliter Tampon density (grams per milliliter)=tampon weight (grams)/tampon volume Secondary Desorption Performance The amount and placement of fluid that is desorbed from a secondary absorbent by the tampon pledget is measured after exposing the secondary to test fluid for a specified amount of time. The secondary wicks the test liquid vertically along its length and is subsequently desorbed by the pledget. The amount of liquid in the bottom portion (by mass) of the pledget is compared to the total amount of liquid in the pledget and reported as % Secondary Desorption. All measurements are performed in a laboratory maintained at 23° C.±2° C. and 50%±2% relative humidity.

Test samples are removed from their outermost packaging and wrapper, then conditioned in a room maintained at 23° C.±2° C. and 50%±2% relative humidity for at least 2 hours prior to testing. The tampon is expelled from its applicator, if present, and the pledget is unfolded/uncompressed and gently flattened by hand. The secondary absorbent is cut at a distance of 20 mm from the edge of the pledget where it is attached and then carefully removed from the pledget after which the mass is measured and recorded as Secondary$_{Dry}$ to the nearest 0.01 g. The longitudinal direction of the tampon is along the axis between the insertion end and the withdrawal end. Empirically determine the longitudinal center of mass of the pledget (i.e. after removing the secondary absorbent) by laterally bisecting the pledget such that the top portion and the bottom portion have equal mass to the nearest±0.1 g.

On a separate test sample, mark the longitudinal center of mass as determined above. The secondary absorbent is straightened perpendicular to the pledget and cut at a distance of 20 mm from the edge of the pledget where it is attached. If the secondary does not extend 20 mm from the edge of the pledget, leave at length and cut the removal cord at the distal edge of the secondary. A mark is then made on the remaining portion of the secondary absorbent at a distance of 5 mm from the cut end. The length of secondary absorbent that is in contact with the pledget is measured and recorded.

The test liquid is prepared by adding 1% w/v sodium chloride and 0.1% w/v FD&C 40 red dye (both reagents available from VWR International) to distilled water. Fill a crystallization dish (e.g. Kimax 90×50 mm, available from VWR International, or equivalent) to within 10 mm of its upper edge with test liquid. Place the dish of test liquid onto a top-loading balance accurate to the nearest 0.01 g. Measure the mass of the dry, marked test sample and record its mass as $Pad_{Dry}$ to the nearest 0.01 grams. Vertically suspend the dry test sample over the bath of test liquid, with the end containing the secondary absorbent oriented towards the liquid. A suitable way to suspend the test sample is to attach a large binder clip to about 5.0 mm of the pledget sample at the insertion end (end opposite of the secondary) and attach to a ring stand. Set a timer for 120 seconds. Gently lower the test sample towards the surface of the test liquid until 5.0 mm of the secondary absorbent has been submerged into the liquid. As soon as the secondary absorbent begins to wick liquid (e.g. balance reading indicates weight loss), start the timer. At 120 seconds, raise the test sample out of the test liquid and remove it from its holder Immediately measure the mass of the wet test sample and record its mass as $Pad_{Wet}$ to the nearest 0.01 g. Using scissors, immediately cut the sample laterally at the mark that denotes its center of mass. Measure the mass of the bottom portion of the wet test sample (the portion containing the secondary absorbent) and record its mass as Bottom $Portion_{Wet}$ to the nearest 0.01 g. Carefully remove the secondary absorbent from the bottom portion of the wet test sample then measure and record its mass as $Secondary_{Wet}$ to the nearest 0.01 g. Calculate % Secondary Desorption as follows and report to the nearest 0.1%.

% Secondary Desorption=[Bottom Portion Uptake (g)/Total Uptake (g)]*100 where Bottom Portion Uptake (g)=[Bottom $Portion_{Wet}$ (g)–$Secondary_{Wet}$ (g)–½ $Pad_{Dry}$ (g)–½ $Secondary_{Dry}$ (g)]

and Total Uptake (g)=[$Pad_{Wet}$ (g)–$Pad_{Dry}$ (g)]

In like fashion, repeat for a total of three replicate test samples. Calculate the arithmetic mean and report "Percent Secondary Desorption" to the nearest 0.1%.

Z-Cluster Measurement

The micro-CT Z-Cluster measurement method measures the area of Z-direction oriented fiber clusters in a primary absorbent member of a tampon pledget absorbent material sample. It is based on analysis of a 3D x-ray sample image obtained on a micro-CT instrument (a suitable instrument is the Scanco μCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and reconstruction of the raw data into a 3D image. The 3D image is then analyzed using image analysis software (suitable image analysis software are MATLAB available from The Mathworks, Inc., Natick, Mass., and Avizo Lite available from Visualization Sciences Group/FEI Company, Burlington, Mass., or equivalents) to identify and segment out clusters of Z-direction fibers, and measure their areas.

Sample Preparation:

To obtain a sample for measurement from a compressed tampon in a self-sustaining form, carefully spread open the absorbent material into a substantially planner configuration and die cut or punch out a circular piece with a diameter of 10 mm The sample is relaxed into an uncompressed state using a small amount of deionized (DI) water pipetted evenly over the surface of the specimen, and allowed to air dry fully prior to analysis. The specific amount of DI water used is determined from the ratio of the lower limit of the industry standard capacity range for the product to the dry mass of the tampon according to the following equation:

$$\frac{\text{Lower Limit of Absorbent Capacity (g)}}{\text{Mass of Tampon (g)}} = \frac{DI \text{ Water to Pipette on Surface (g)}}{\text{Mass of Die Cut Sample (g)}}$$

For example, "regular absorbency" tampons are labeled with an absorbent capacity range of 6 to 9 grams. The lower limit being 6 g. Therefore, for a tampon with a mass of 2 g the amount of DI water (g) to pipette on the sample surface would be equal to 3 (g/g) multiplied by the mass of the die cut sample (g).

A sample may be cut from any location that is representative of the bulk of the tampon pledget material. When selecting a location for sampling, care should be taken to avoid regions of the absorbent pledget where the material structure may have been so significantly crushed during the product making process that it cannot be fully relaxed, as well as any excessive folds, wrinkles or tears.

Image Acquisition:

The micro-CT instrument is set up and calibrated according to the manufacturer's specifications. The sample is placed into the appropriate holder, between two rings of low density material, which have an inner diameter of at least 8 mm. This will allow the central region of the sample to lay horizontal and be scanned without having any other materials directly adjacent to its upper and lower surfaces. Analysis will be performed within this central region. A single 3D dataset of contiguous 3 μm (microns) isotropic voxels is collected. The 3D dataset is centered on the central analysis region, having dimensions of 15 mm on each side in the XY-plane and a sufficient number of slices to fully include the Z-direction of the sample. Images are acquired with the source at 45 kVp and 133 μA with no additional low energy filter. These current and voltage settings may be optimized to produce the maximum contrast in the projection data with sufficient x-ray penetration through the sample, but once optimized held constant for all substantially similar samples. A total of 3200 projection images are obtained with an integration time of 750 ms and 3 averages. The projection images are reconstructed into a 3D dataset having an isotropic spatial resolution of 3 µm (microns), and saved in 16-bit RAW format to preserve the full detector output signal for analysis.

Image Processing:

The 3D dataset is loaded into the image analysis software, and trimmed (cropped) to a rectangular prism 3D image of the analysis region by removing the surrounding holder and the low density mounting material from the 3D dataset. Trimming is performed such that the maximum amount of the sample in the analysis region is retained in the 3D image, and the empty space above and below the sample is minimized. The trimmed 3D image is scaled from 16-bit to 8-bit, and thresholded using Otsu's method, which calculates the threshold level that minimizes the weighted intra-class variance, to separate and remove the background signal due to air, but maintain the signal from the fibers within the sample image. This generates a binary 3D data set where fiber voxels are assigned a value of 1 (one) and void voxels are assigned a value of 0 (zero).

The 3D image is oriented so that the upper surface is as close to parallel with the XY-plane as possible.

The Z-direction fibers are identified and distinguished using a Z-direction vector, such that given an XY-plane position, a typical Z-direction vector traveling from the top of the 3D image to the bottom will first pass through the upper surface, and then pass through underlying sample fibers. As an individual Z-direction vector travels from the top of the 3D image downward there may be a series of contiguous fiber voxels, with a value of 1, in the vector as it passes through the sample. A contiguous series of fiber voxels will be defined as a run of fiber voxels, and its length in voxels recorded. For every Z vector in the (X, Y) plane an average fiber run length is determined for that vector by dividing the sum of the individual run lengths by the number of runs along that vector. This process is repeated as a Z-direction vector is passed through every XY-plane position in the 3D image. The average run lengths create a 2D array which can be viewed as an image, where the value at each XY position is equal to the average run length of its corresponding position in the XY-plane of the analyzed 3D image. Higher average run values in the "Average Fiber Run Length" image indicate the presence of fibers oriented in the Z-direction.

The mean and standard deviation of the all the average fiber run length values in the 2D image is calculated. The "Average Fiber Run Length" image is thresholded at a value of the mean plus two standard deviations to generate a binary image identifying the locations of the fibers with the most significant orientation in the Z-direction.

A connected components algorithm is executed on the thresholded 2D average run length image, which groups, or clusters, together the Z-direction voxels that are 8-connected (touching one of their edges or corners) to neighboring Z-direction voxels. The total number of pixels in each of the Z-direction clusters is calculated, and the pixel count in the three largest Z-Clusters is recorded. The Z-Cluster count is converted to area by multiplying the cluster pixel count by 9 µm$^2$, the XY area of each pixel, and then converted to mm$^2$. The area of the third largest Z-Cluster is recorded to the nearest 0.01 mm$^2$. The average area of the top three Z-Cluster is calculated and recorded to the nearest 0.01 mm$^2$.

A total of three substantially similar replicate tampon pledget material samples are analyzed in like manner, and the statistical mean of the three recorded Area of the Third Largest Z-Cluster and the Average Area of the Top Three Z-Clusters is each reported to the nearest 0.01 mm$^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 millimeters" is intended to mean "about 40 millimeters."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent tampon comprising:
a primary absorbent member having an insertion end and a withdrawal end disposed opposite the insertion end, a top adjacent the insertion end, a bottom adjacent the withdrawal end, and a middle disposed between the top and the bottom, the primary absorbent member comprising at least one layer of fibrous absorbent material, the primary absorbent member and/or the at least one layer thereof having been needlepunched to an extent sufficient to impart the primary absorbent member with a Z-direction fiber integration reflecting either or both of:
an area of a third largest Z-cluster of greater than 0.01 mm^2; and
an average area of top three clusters of at least 0.02 mm^2; and
a secondary absorbent member attached to the primary absorbent member and extending outboard of the withdrawal end of the primary absorbent member.

2. The absorbent tampon of claim 1, wherein the primary absorbent member comprises between about 50 percent to about 100 percent trilobal rayon fibers and between 0 percent and 50 percent round rayon fibers.

3. The absorbent tampon of claim 2, wherein the trilobal rayon fibers have a decitex of between 3.0 and about 4.5.

4. The absorbent tampon of claim 1, wherein the primary absorbent member has a basis weight of between about 200 gsm to about 1200 gsm.

5. The absorbent tampon of claim 4, wherein the primary absorbent member comprises only one layer of absorbent material.

6. The absorbent tampon of claim 4, wherein the primary absorbent member comprises more than one layer of absorbent material.

7. The absorbent tampon of claim 6, wherein each of the layers of absorbent material is spunlaced.

8. The absorbent tampon of claim 1, wherein the primary absorbent member exhibits an area of the third largest cluster of greater than 0.03 mm^2.

9. The absorbent tampon of claim 1, wherein the primary absorbent member exhibits an average area of the top three clusters of at least 0.03 mm^2.

10. The absorbent tampon of claim 1, wherein the tampon exhibits a wet weight percentage fluid in the bottom portion of greater than 60 percent when measured in accordance with the Secondary Desorption Performance method.

11. The absorbent tampon of claim 1, wherein the tampon exhibits a wet weight percentage fluid in the bottom portion of greater than 63 percent when measured in accordance with the Secondary Desorption Performance method.

12. The absorbent tampon of claim 1, wherein the primary absorbent member comprises 100 percent cotton fibers.

13. The absorbent tampon of claim 1, wherein the primary absorbent member comprises a cotton/rayon blend wherein the cotton is present at less than 100 percent.

14. The absorbent tampon of claim 13, wherein the cotton is present in an amount of less than about 76 percent.

15. The absorbent tampon of claim 13, wherein the cotton is present in an amount of less than about 51 percent.

16. The absorbent tampon of claim 13, wherein the cotton is present in an amount of less than about 26 percent.

\* \* \* \* \*